(12) United States Patent
Hirsch

(10) Patent No.: US 7,611,354 B2
(45) Date of Patent: *Nov. 3, 2009

(54) COOLING DEVICE AND METHOD FOR INTRAORAL DEVICE ILLUMINATION SOURCE

(75) Inventor: James A. Hirsch, Santa Barbara, CA (US)

(73) Assignee: Innerlite, Inc., Santa Barbara, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 11/859,979

(22) Filed: Sep. 24, 2007

(65) Prior Publication Data

US 2008/0008977 A1    Jan. 10, 2008

Related U.S. Application Data

(63) Continuation of application No. 11/223,098, filed on Sep. 9, 2005, now Pat. No. 7,287,981, which is a continuation-in-part of application No. 10/375,230, filed on Feb. 27, 2003, now Pat. No. 6,974,321, which is a continuation-in-part of application No. 10/006,732, filed on Nov. 15, 2001, now Pat. No. 6,575,746, which is a continuation of application No. 09/777,491, filed on Feb. 5, 2001, now Pat. No. 6,338,627, which is a continuation of application No. 09/490,923, filed on Jan. 25, 2000, now abandoned, which is a continuation of application No. 09/193,916, filed on Nov. 17, 1998, now Pat. No. 6,022,214.

(51) Int. Cl.
*A61C 17/06* (2006.01)

(52) U.S. Cl. ........................................... 433/93

(58) Field of Classification Search ............... 433/29, 433/91, 95, 96; 604/902; 362/800, 804
See application file for complete search history.

(56) References Cited

U.S. PATENT DOCUMENTS

| | | | |
|---|---|---|---|
| 1,122,086 A | 12/1914 | Dunlap | |
| 2,510,125 A | 6/1950 | Lawrence | |
| 3,881,254 A | 5/1975 | Epsteen | |
| 4,167,814 A | 9/1979 | Schubert | |
| 4,259,067 A | 3/1981 | Nelson | |
| 4,495,945 A | 1/1985 | Liegner | |
| 4,592,344 A | 6/1986 | Scheer | |
| 4,643,172 A | 2/1987 | Taff et al. | |
| 4,759,349 A * | 7/1988 | Betz et al. | 604/27 |
| 4,802,851 A | 2/1989 | Rhoades | |
| 4,865,545 A | 9/1989 | La Rocca | |
| 4,975,057 A | 12/1990 | Dyfvermark | |
| 4,992,046 A | 2/1991 | Sharp | |
| 4,996,976 A | 3/1991 | Nakagawa | |
| 5,009,595 A | 4/1991 | Osborn | |

(Continued)

*Primary Examiner*—Ralph A Lewis
(74) *Attorney, Agent, or Firm*—Stephen C. Beuerle; Procopio Cory Hargreaves & Savitch LLP

(57) ABSTRACT

A method of using a heat sink device with an intraoral illumination device includes inserting an intraoral illumination device at least partially in a patient's mouth, connecting a heat sink device to the intraoral illumination device, the heat sink device including an illumination device that emits light and heat when activated and a heat sink member thermally coupled to the illumination device; activating the illumination device so that light is transmitted to the intraoral illumination device and into the patient's mouth, aspirating fluid from the patient's mouth at negative pressure; and causing aspirated fluid to flow past the heat sink member at negative pressure so that heat is removed from the heat sink member, causing the illumination device to be cooled.

9 Claims, 13 Drawing Sheets

U.S. PATENT DOCUMENTS

| | | |
|---|---|---|
| 5,071,347 A | 12/1991 | McGuire |
| 5,078,602 A | 1/1992 | Honoshoesky |
| 5,152,686 A | 10/1992 | Duggan et al. |
| 5,232,362 A | 8/1993 | Kanas |
| 5,281,134 A | 1/1994 | Schultz |
| 5,462,435 A | 10/1995 | Young |
| 5,513,986 A | 5/1996 | Feltham et al. |
| 5,588,836 A | 12/1996 | Landis et al. |
| 5,634,711 A * | 6/1997 | Kennedy et al. ............ 362/119 |
| 5,762,496 A | 6/1998 | Albertsson et al. |
| 5,769,635 A | 6/1998 | Eldreth |
| 5,873,718 A | 2/1999 | Sullivan |
| 6,022,214 A | 2/2000 | Hirsch et al. |
| 6,338,627 B2 | 1/2002 | Hirsch et al. |
| 6,575,746 B2 | 6/2003 | Hirsch et al. |
| 6,611,110 B1 | 8/2003 | Fregoso |
| 7,021,798 B2 | 4/2006 | Tsimerman et al. |
| 7,287,981 B2 * | 10/2007 | Hirsch ........................ 433/29 |
| 2005/0171408 A1 | 8/2005 | Parker |

* cited by examiner

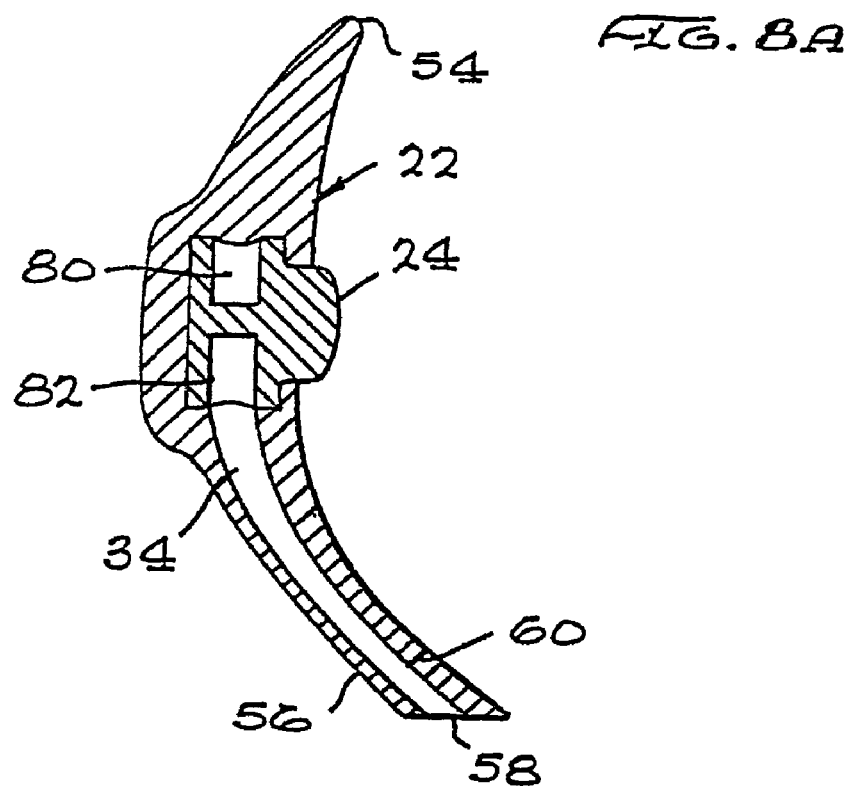
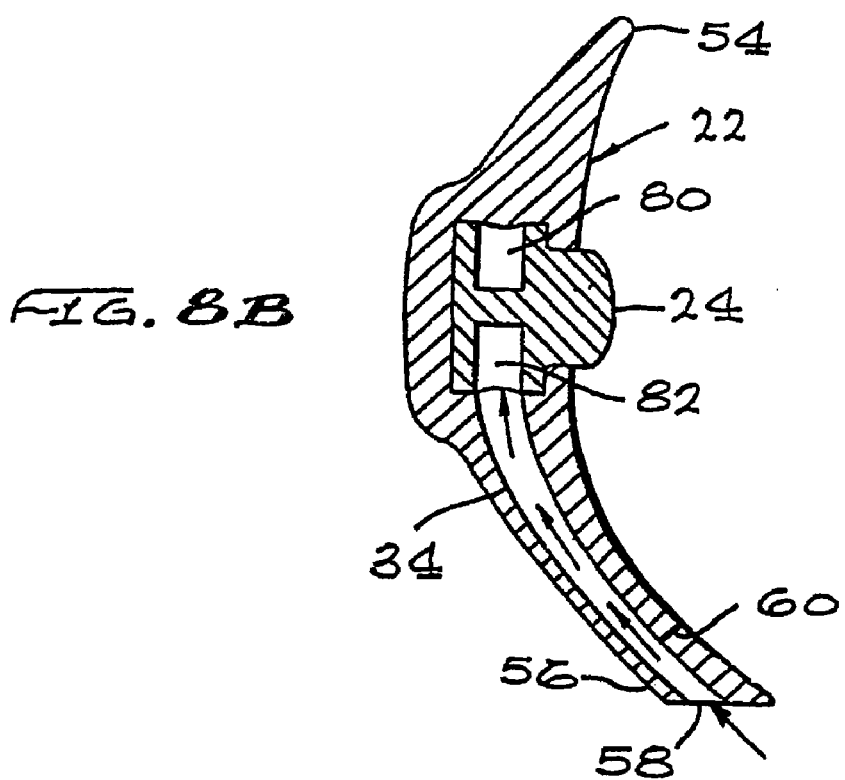

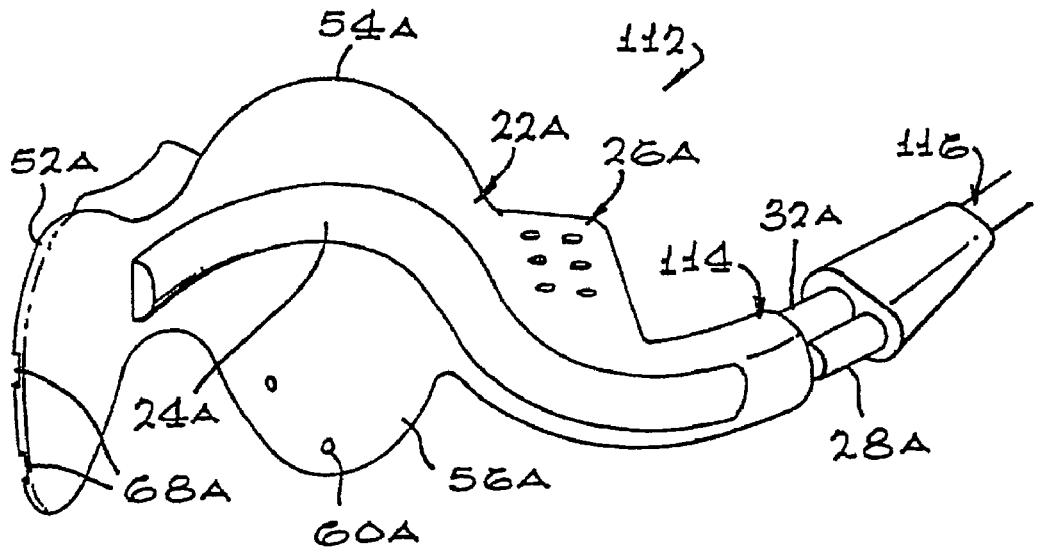
FIG. 9
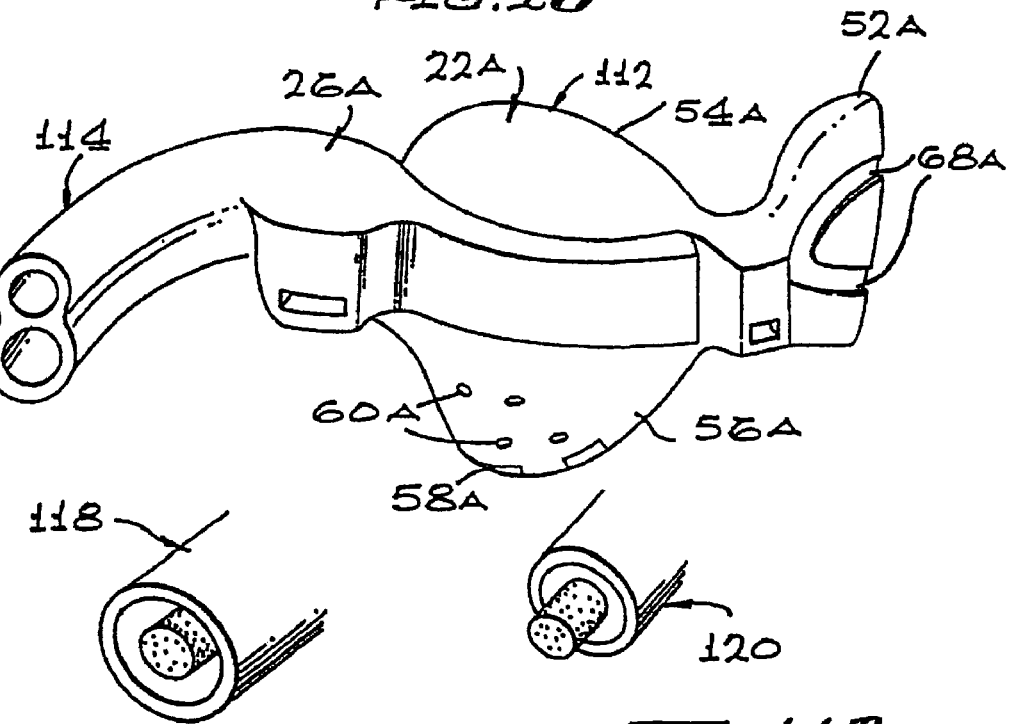
FIG. 10
FIG. 11A
FIG. 11B

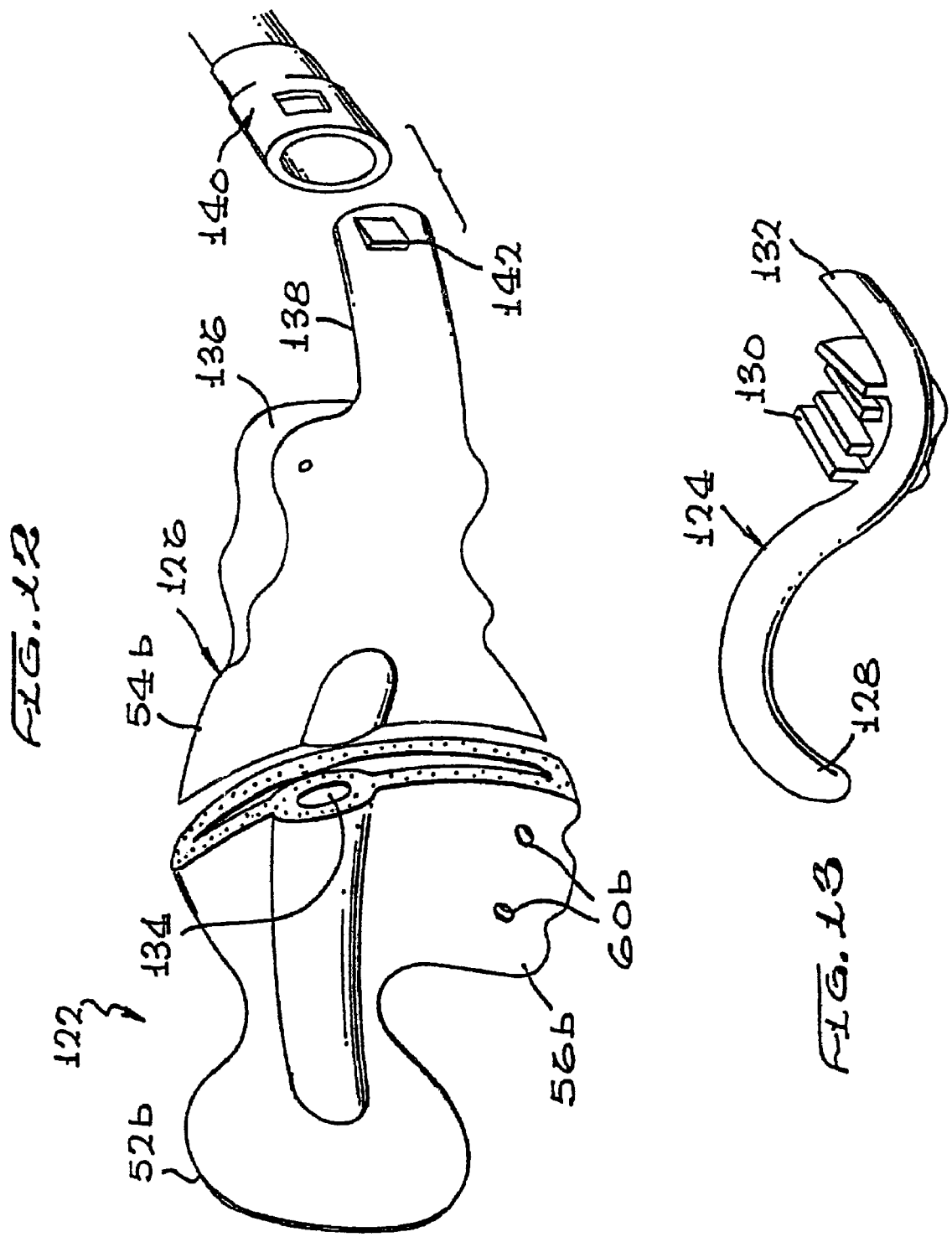

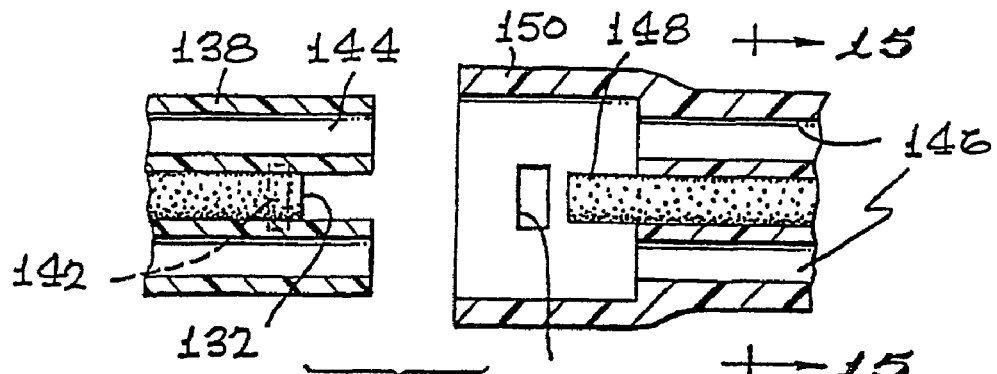
FIG. 14
FIG. 15
FIG. 16
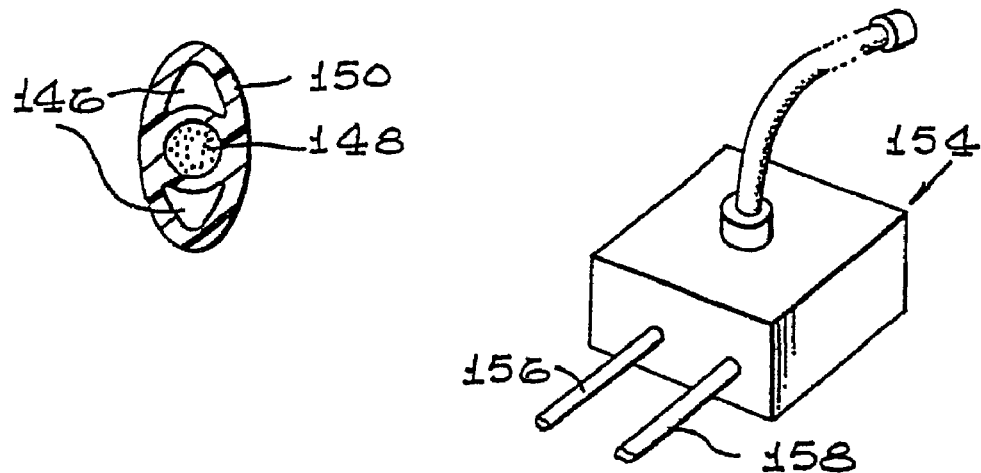
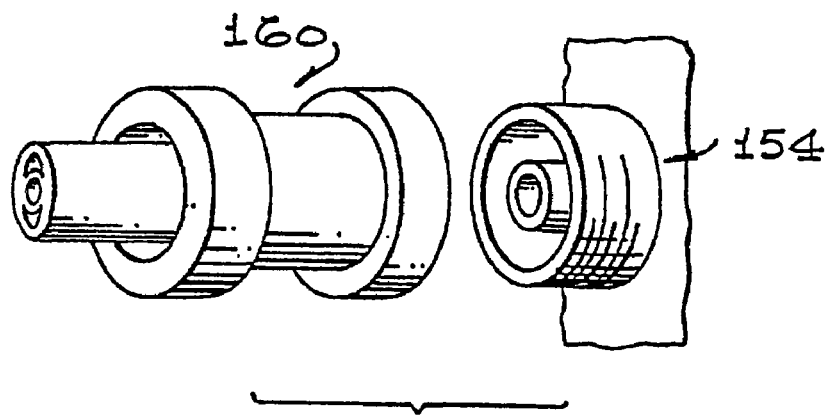
FIG. 17

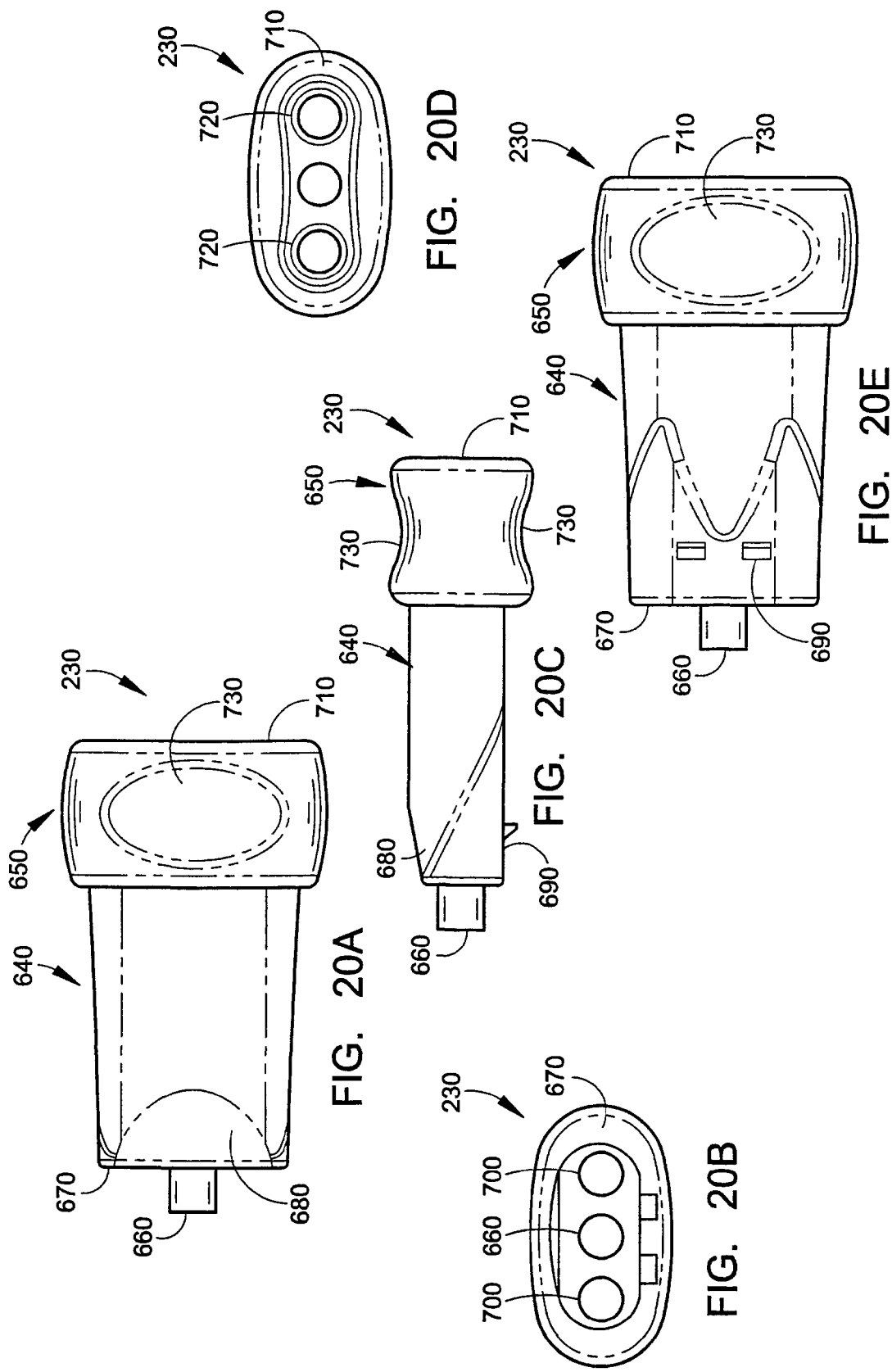

COOLING DEVICE AND METHOD FOR INTRAORAL DEVICE ILLUMINATION SOURCE

CROSS-REFERENCE TO RELATED APPLICATIONS

This is a continuation of pending prior application Ser. No. 11/223,098 filed Sep. 9, 2005, which is a continuation-in-part of pending prior application Ser. No. 10/375,230 filed Feb. 27, 2003, which is a continuation-in-part of pending prior application Ser. No. 10/006,732 filed Nov. 15, 2001, which issued on Jun. 10, 2003 as U.S. Pat. No. 6,575,746, which is a continuation of prior application Ser. No. 09/777,491 filed Feb. 5, 2001 which issued on Jan. 15, 2002 as U.S. Pat. No. 6,338,627, which is a continuation of prior application Ser. No. 09/490,923 filed on Jan. 25, 2000, now abandoned, which is a continuation of prior application Ser. No. 09/193,916 filed on Nov. 17, 1998, which issued on Feb. 8, 2000 as U.S. Pat. No. 6,022,214. These applications, patents are incorporated by reference as though set forth in full.

FIELD OF THE INVENTION

The invention relates to dental appliances for illuminating and/or vacuum suction of the mouth, and accessories and methods therefor.

BACKGROUND OF THE INVENTION

Illuminating the interior of a dental patient's mouth during dental examination and/or operation is difficult because the patient's mouth must be illuminated through a narrow opening, i.e., the patient's mouth, and the dental operator must work in close proximity to the mouth, often blocking the light source. Proper illumination is essential for dental examination and/or operation.

The oral cavity is typically illuminated by a focused light source mounted approximately two to three feet above a dental chair that the patient rests on. The light source is configured to direct light onto and into the patient's mouth. The amount of light entering the oral cavity using this type of lighting is somewhat limited due to the fact that the light source is remote from the patient's mouth. Additionally, the dental operator must often position oneself or his or her instruments between the light source and the patient's mouth to properly view the patient's mouth, blocking light from entering the mouth. The blocking of light casts an effective shadow in the patient's mouth or in areas of the patient's mouth such as certain teeth.

In order to inhibit this blocking or shadowing, fiber optic lighting has been incorporated into handheld dental instruments. Typically multiple fiber optic strands extend longitudinally along the instrument and include a light outlet end configured to direct light towards the end of the instrument. However, this type of lighting has a number of drawbacks. Light is only directed on a limited area in the mouth and does not provide illumination for the entire oral cavity. Additionally, the presence of this type of lighting, typically as an add-on feature on the instrument interferes with the comfortable and proper use of the instrument. The fiber optic bundles also-degrade over time because the fiber optics and instrument go through autoclaving numerous times. Components of the instrument, e.g., turbines, may be easily changed once degraded but the fiber optic bundles can not.

Other devices have been designed specifically for illuminating a patient's teeth, but these devices suffer from any or all of the following drawbacks: inadequate illumination of the patient's teeth, and interference with other dental instruments used during the examination and/or operation.

The present inventors have recognized the desirability of using LED(s) or other illumination sources in conjunction with and/or adjacent to intraoral illumination and aspiration devices. A problem with the use of LED(s) or other illumination sources in this manner is that these illumination device(s) emit heat, which can damage the device or accessories and be uncomfortable or hazardous for the patient.

SUMMARY OF THE INVENTION

An aspect of the invention involves a method of using a heat sink device with an intraoral illumination device. The method includes inserting an intraoral illumination device at least partially in a patient's mouth, connecting a heat sink device to the intraoral illumination device, the heat sink device including an illumination device that emits light and heat when activated and a heat sink member thermally coupled to the illumination device; activating the illumination device so that light is transmitted to the intraoral illumination device and into the patient's mouth, aspirating fluid from the patient's mouth at negative pressure; and causing aspirated fluid to flow past the heat sink member at negative pressure so that heat is removed from the heat sink member, causing the illumination device to be cooled.

Another aspect of the invention involves a method of using a heat sink with an intraoral illumination device. The method includes providing a heat sink with one or more LEDs to illuminate the patients mouth through the intraoral illumination device, the one or more LEDs emitting heat when activated, the heat sink including a fluid delivery lumen for delivering aspirated cooling fluid under a vacuum condition in the region of the one or more LEDs; and removing heat from the region of the one or more LEDs by causing aspirated fluid under a vacuum condition to flow through the region of the one or more LEDs.

A still further aspect of the invention involves a heat sink device for use with an intraoral illumination device configured for illumination of and aspiration of fluid from the patient's mouth. The heat sink device includes an illumination device configured to emit light and heat when activated; and a heat sink member thermally coupled to the illumination device and configured to receive aspirated fluid from the patient's mouth at negative pressure so that heat is removed from the heat sink member, causing the illumination device to be cooled.

Other, more particular features and advantages of the inventions are set forth in the following detailed description and drawings.

BRIEF DESCRIPTION OF THE DRAWINGS

The drawings illustrate both the design and utility of preferred embodiments of the present invention, in which similar elements are referred to by common reference numbers, wherein:

FIG. 4 is a rear perspective view of the intraoral illumination device illustrated in FIG. 1;

FIGS. 8A and 8B are cross-sectional views of the intraoral illumination device illustrated in FIG. 1 and illustrate the evacuation of fluids through the evacuation system of the device;

FIG. 10 is a rear perspective view of the intraoral illumination device illustrated in FIG. 9;

FIG. 11a is a partial perspective view of an alternative embodiment of an integrated light carrier and vacuum tube connector;

FIG. 11b is a partial perspective view of an alternative embodiment of an integrated light carrier and vacuum tube that the integrated light carrier and vacuum tube connector illustrated in FIG. 11 may be connected with;

FIG. 12 is a front perspective view of an alternative preferred embodiment of the intraoral illumination device and shows the intraoral illumination device in conjunction with a preferred embodiment of a multi-lumen tube;

FIG. 13 is a rear, top perspective view of a preferred embodiment of a light dispersion piece that may be used with the intraoral illumination device illustrated in FIG. 12;

FIG. 14 is a cross sectional view of a connection section of the intraoral illumination device and an end portion of the multi-lumen tube;

FIG. 15 is a cross sectional view of the multi-lumen tube taken along lines 15-15 of FIG. 14;

FIG. 16 is a perspective view of an embodiment of a transition mechanism that may be used to transition a separate light carrier and vacuum tube into the single multi-lumen tube; and FIG. 17 is perspective view of an embodiment of a connector that may be used to couple the transition mechanism to the multi-lumen tube.

FIG. 20A is a front elevational view of the intraoral device adapter illustrated in FIG. 18A.

FIG. 20B is a left side elevational view of the intraoral device adapter illustrated in FIG. 18A.

FIG. 20C is a bottom plan view of the intraoral device adapter illustrated in FIG. 18A.

FIG. 20D is a right side elevational view of the intraoral device adapter illustrated in FIG. 18A.

FIG. 20E is a rear elevational view of the intraoral device adapter illustrated in FIG. 18A.

DETAILED DESCRIPTION OF PREFERRED EMBODIMENTS

An aspect of the invention involves a combined illumination, aspiration and heat sink device for use with an intraoral illumination device. Before describing the combined illumination, aspiration and heat sink device, a number of embodiments of intraoral illumination devices, which represent other aspects of the invention, will first be described.

Figure 1:
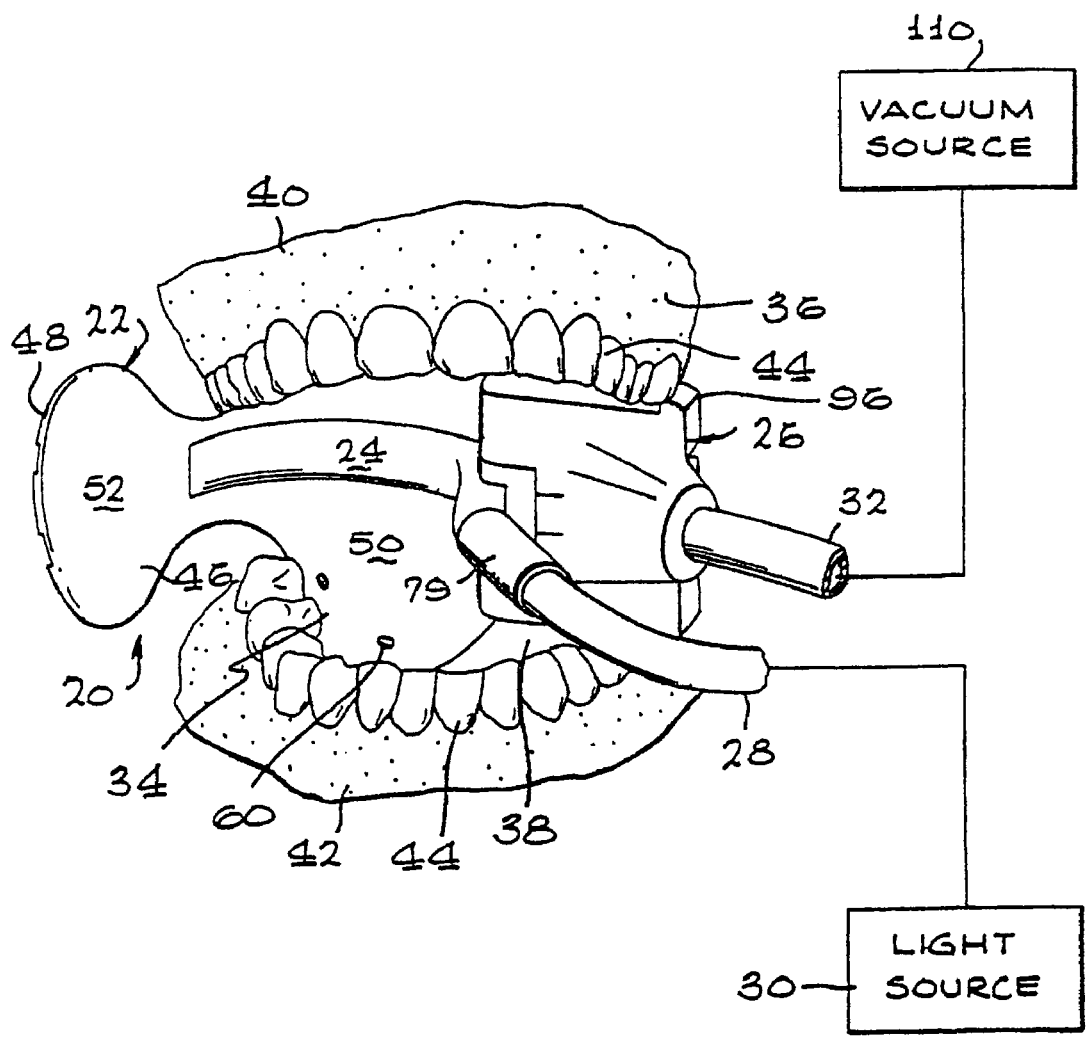
FIG. 1 is a front perspective view of a preferred embodiment of the intraoral illumination device of the present invention shown inside a patient's mouth.
Figure 2:
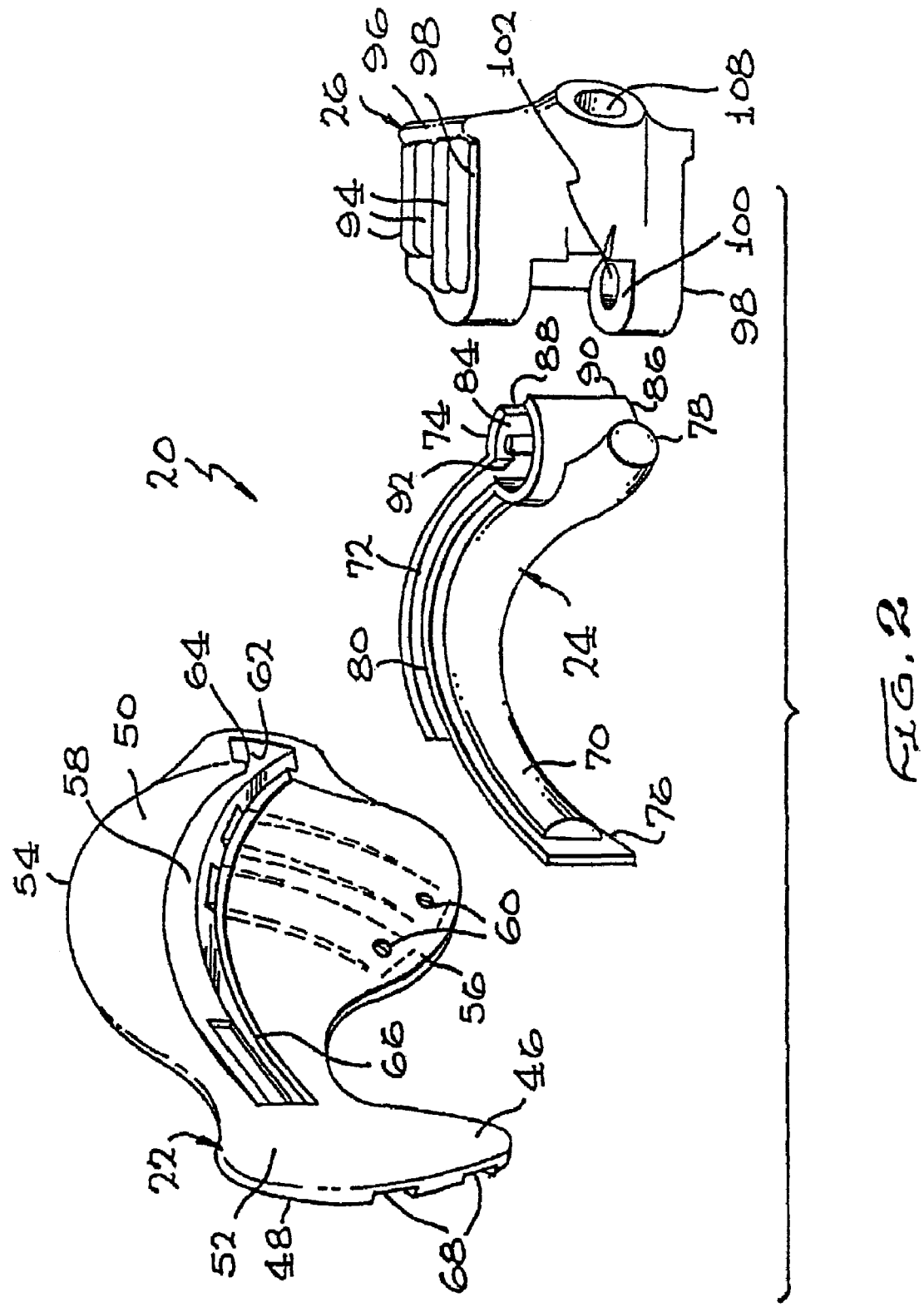
FIG. 2 is a front perspective view of the components of the intraoral illumination device illustrated in FIG. 1 in a disassembled state.
Figure 3:
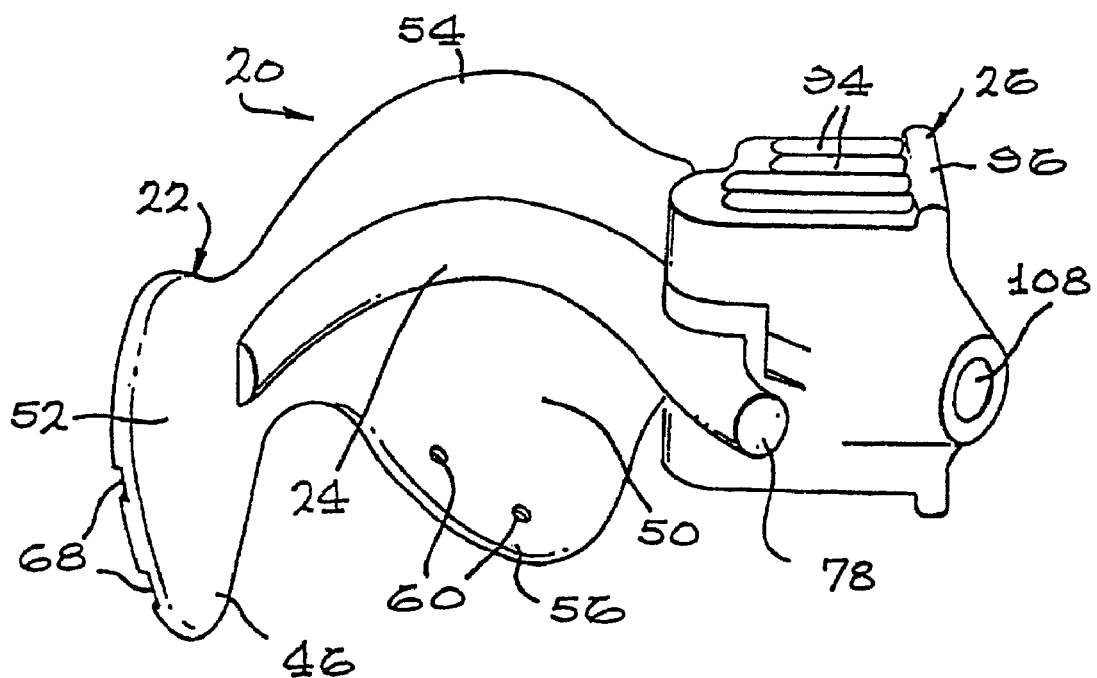
FIG. 3 is a front perspective view of the intraoral illumination device illustrated in FIG. 1.

With reference to FIGS. 1 and 2, an embodiment of an intraoral illumination device, indicated generally by the reference numeral 20, will now be described. The intraoral illumination device 20 generally includes a tongue and cheek retractor 22, a dispersion piece 24, and a bite block or piece 26. The tongue and cheek retractor 22 is a disposable piece, and the dispersion piece 24 and bite piece 26 are sterilizable for reuse. In an alternative embodiment, the entire intraoral illumination device 20 is disposable. The dispersion piece 24 is coupled to a light carrier such as a fiber optic bundle 28 and extraoral light source 30 for illuminating the dispersion piece 24. A fluid evacuation tube 32 is in communication with the bite block 26 and a fluid evacuation system 34 of the device 20 for evacuating fluids from a patient's mouth 36.

The intraoral illumination device 20 will now be described generally in use. The patient opens his or her mouth 36 and a health care provider inserts the device 20 into an intraoral cavity 38 of the patient's mouth 36 between the patient's upper jaw 40 and lower jaw 42. The patient rests his or her jaws 40, 42 during the process to be performed by gently biting on the bite block 26 with his or her rear teeth 44. To help isolate the area of the mouth 36 being worked on and protect the patient's mouth from being injured by the dental tools, the tongue and cheek retractor 22 urges the patient's cheek and tongue away from the area of isolation. Fluids produced in the patient's mouth 36 during the process are removed through the fluid evacuation system 34 of the device 20 and vacuum tube 32. Light transmitted through the light carrier 28 to the dispersion piece 24 is dispersed outward from the dispersion piece 24, towards the front of the patient's mouth, from a rear, central part of the intraoral cavity 38 flooding the patient's mouth with light. Illuminating the area of interest in the patient's mouth in this manner eliminates the aforementioned problems with blocked light or shadowing.

Although this invention has been described in connection with illuminating, isolating, and removing fluids from a patient's mouth for dentistry, it will be readily understood by those skilled in the art how the present invention may have other mouth-related applications where illumination in the mouth is required other than dentistry such as, but not by way of limitation, oral surgery or other dental operations.

With reference to FIGS. 1-7, each of the components of the device 20 will now be described. The tongue and cheek retractor 22 is made of a single molded piece of soft, flexible, biocompatible material such as Pebax, santoprene, or a molded vinyl material. However, it will be readily understood by those skilled in the art that other soft, flexible materials could be used. The tongue and cheek retractor 22 is preferably produced by a gas-assist injection molding process in order to produce the internal vacuum channels described below. However, it will be readily understood by those skilled in the art that other molding processes such as an injection molding process could also be used. As discussed in more detail below, the tongue and cheek retractor 22 may be a separate piece that can be easily added to or removed from the dispersion piece 24. The tongue and cheek retractor 22 also may come in two different main configurations, depending on the side of the mouth being examined and/or operated on, i.e., left side, right side, and different sizes for different size and shaped mouths. The retractor 22 has an inner surface 46 and an outer surface 48.

The retractor 22 includes a curved main body portion 50 and a cheek retractor portion 52.

The main body portion 50 includes an upper roof portion 54 configured to rest against the roof of the patient's mouth 36 during use and a lower tongue retractor portion 56 to keep the tongue protected and retracted. The lower tongue retractor portion 56 helps to isolate the area of interest in the mouth 36 and protect the tongue from instruments such as dental drills during the dental procedure. The tongue retractor portion 56 includes internal evacuation channels 58. Evacuation holes 60 on both the inner surface 46 and outer surface 48 of the tongue retractor portion 56 communicate with the evacuation channels 58. The evacuation channels 58 terminate at an upper part of the tongue retractor portion 56 at a main receiving channel 62. The main receiving channel 62 includes a lip 64 for slidably receiving the dispersion piece 24. A pair of shallow evacuation channels 66 extend along a portion of the main receiving channel 62. Evacuation holes 66 allow communication of the evacuation channels 58 with the outer surface 48 of the retractor 22.

The cheek retractor portion 52 has a curved, fish-tail shape and includes a pair of evacuation channels 68 exposed to the outer surface 48 of the retractor 22 that communicate with the evacuation channels 66. The cheek retractor portion 52 protects adjacent cheek tissue during the dental procedure and helps to isolate the area of interest of the mouth 36 during the dental procedure by retracting the cheek tissue.

The dispersion piece 24 is an illumination member and is preferably made of a single, injection-molded piece of light-dispersive, biocompatible, sterilizable material. The dispersion piece 24 may be made of a rigid material such as acrylic or a flexible material such as a molded flexible urethane. However, it will be readily understood by those skilled in the art that other clear, flexible or rigid materials may be used. The dispersion piece 24 preferably has an arcuate, semi-circular shape and includes a generally U-shaped dispersion lens 70, a fluid evacuation portion 72, and a pivot portion 74.

The dispersion lens 70 includes a flange 76 that is slidably received by the lip 64 of the main receiving channel 62 for attaching the dispersion piece 24 to the tongue and cheek retractor 22. The dispersion lens 70 may have a composition that is varied, e.g., graduated, to control the amount of dispersion in different areas of the lens 70 and evenly distribute the overall rumination. This helps prevent "hot spots" in the dispersion lens 70, i.e., areas of the lens 70 that emit a greater concentration of light. These "hot spots" make it difficult for the health care provider to observe the patient's mouth. For example, in the area where the fiber optic bundle 28 connects with the dispersion lens 70, there may be a less textured composition to inhibit the breaking up of internal reflections, and a progressively more textured composition as one approaches the opposite end of the lens 70. It will be readily understood by those skilled in the art that the tongue and cheek retractor 22 or other covering may have a similar varied composition to control dispersion of light in a similar manner.

The dispersion lens 70 optically communicates with the light carrier 28 through a stem 78 and a separate connector 79. The light carrier 28 is preferably adapted to be directly connected to a commercially available illumination source as those found in most dentist offices or adapted to be connected to such sources through a connector or transition mechanism (not shown). Alternatively, the stem 78 and connector 79 may be a single integrated molded piece. The stem 78 serves as a light coupling between the light carrier 28 and dispersion lens 70.

In use, light shines outward from the lens 70 and is scattered by the lens 70 to illuminate the patient's mouth 36. When in place, the configuration of the device 20 causes light to be transmitted by the dispersion lens 70 from a central, rear part of the intraoral cavity, substantially between the patient's rear teeth 44. The U-shaped dispersion lens 70 has a generally 180 degree arcuate shape. This generally 180 degree arcuate shape and the dispersional qualities of the lens 24 spread the total area of illumination. Illuminating the mouth from the central, rear part of the intraoral cavity and the above-described attributes of the lens 24 eliminate shadows caused by a single-point light source, and shadows caused by the health care provider or equipment used by the health care provider. The intraoral illumination device 20 may replace or be used with dental instruments including fiber optic lighting.

The fluid evacuation portion 72 includes a first main evacuation channel 80 and a second main evacuation channel 82 for evacuating fluids from the device 20.

The pivot portion 74 includes a first well 84 and a second well 86 that respectively communicate with the first and second main evacuation channels 80, 82. A first recess 88 and second recess 90 are used to further communicate the wells 84, 86 with the fluid evacuation tube 32 in a manner to be described. Respective pivot pins 92 extend from each well 84, 86.

The bite block 26 is made of a single piece of biocompatible, sterilizable material such as rubber. The bite block 26 may be formed by a compression molding process, a transfer molding process, a casting process, an injection molding process, or similar process. The bite block 26 includes ribs 94 and ridges 96 along opposite faces 98 of the bite block 26. The ribs 94 and ridges 96 help to prevent the bite block 26 from slipping between the molar and bicuspid teeth 44 of the patient. When held or engaged between the patient's teeth, the bite block 26 functions to hold the dispersion lens 70 in a rear, central part of the interior cavity of the patient's mouth so that light can be transmitted outward therefrom for illuminating the interior cavity.

A pivot portion 100 of the bite block 26 includes opposite receiving grooves 102. The receiving grooves 102 receive the pivot pins 92 of the dispersion lens 70 for pivotally connecting the dispersion piece 24 and tongue and cheek retractor 22 to the bite block 26. This pivoting ability allows the health care provider to adjust, i.e., swivel, the dispersion piece 24 and tongue and cheek retractor 22 to accommodate patients with different arch widths.

The intraoral illumination device 20 may also come in different sizes and to accommodate different mouth sizes and shapes.

In an alternative embodiment of the device (FIGS. 9, 10, 12), the dispersion piece 24 and bite piece 26 are not pivotally connected to each other, i.e., the connection is fixed. If the connection is fixed, it is especially important to provide the intraoral illumination device 20 in different configurations and sizes to accommodate the different mouth sizes and shapes. Likewise, if the device (FIGS. 9, 10, 12) is disposable, it is important to provide the device in different configurations and sizes to accommodate the different mouth sizes and shapes.

The bite block 26 includes an internal evacuation channel 104 in communication with the first and second main evacuation channels 80, 82 through the first and second recesses 88, 90, respectively, for evacuating fluids from the patient's mouth 36 during the procedure. The recesses 88, 90 are sized to allow constant sealed communication of the internal evacuation channel 104 with the main evacuation channels 80, 82, regardless of the pivoted position or articulation of the dispersion piece 24 and tongue and cheek retractor 22. External evacuation channels 106 are located on the outside of the bite block 26 and are in communication with the internal evacuation channel 104 for further removal of fluids from the mouth 36. Fluids are vacuumed from the internal evacuation channel 104 of the bite block 26 through an exit port 108.

During use, the patient rests his or her jaws 40, 42 on the faces 98 of the bite block 26, eliminating the need to strain one's jaw muscles to keep the mouth open. This resting of the jaws 40,42 causes the bite block 26 to hold the dispersion piece 24 and tongue and cheek retractor 22 in the rear, central part of the oral cavity. The bite block 26 also serves as an evacuation exit for fluids and as a means for positioning and holding the dispersion piece 24 and tongue and cheek retractor 22 in the oral cavity.

Before inserting the intraoral illumination device 20 in the patient's mouth 36, the heath care provider ensures that the intraoral illumination device 20 is configured for examining and/or operating on the specific area of the patient's mouth of interest, i.e., right side, left side. If the device 20 includes a replaceable tongue and cheek retractor 22, the tongue and cheek retractor 22 used with the device 20 should be the proper configuration and size for the area of the patient's mouth of interest. A tongue and cheek retractor 22 specific to the size and area of the mouth of interest is added to the dispersion piece 24 by sliding the flange 76 of the dispersion lens 70 into the main receiving channel 62 of the tongue and cheek retractor 22. Alternatively, if the device is disposable (FIGS. 9, 10, 12), a device specific to the size and area of the mouth of interest is used. The device is then inserted into the patient's mouth 36 in the manner described above. If the provider desires to examine the opposite side of the patient's mouth 36, the health care provider removes the device 20 from the patient's mouth, removes the tongue and cheek retractor 22 from the dispersion piece 24 by sliding the retractor 22 off of the flange 76, flips the bite block 26 and dispersion piece 24, which are common for both sides of the mouth 36, adds a new tongue and cheek retractor 22 configured for use with the opposite side of the mouth 36, and places the device 20 back into the patient's mouth 36 so that bite block 26 resides in the opposite side of the patient's mouth 36. Alternatively, if the device is disposable, the health care provider must ensure that a device adapted for use with the size and side of the mouth being examined is used. After use of the intraoral illumination device 20, the tongue and cheek retractor 22 is disposed and the bite piece 26 and dispersion piece 24 are autoclaved or sterilized by a similar method. If a disposable intraoral illumination device is used, the device is simply disposed of in a proper biohazardous receptacle.

With reference to FIGS. 8A and 8B, the fluid evacuation system 34 of the intraoral illumination device 20 will now be described in greater detail. During dental examination and/or operation, a number of fluids, e.g., saliva from the parotid gland, blood, water from the dental equipment, are produced in the patient's mouth 36. It is important to remove these fluids for the comfort of the patient, to prevent fluids and material from being aspirated into the throat or lungs of the patient, and to assist the health care provider in observing and/or operating within the patient's mouth 36. The fluid evacuation system 34 removes fluids from all areas of the mouth, e.g., operating side, vestibule area on the operation side, the lingual vestibule (along the side of the tongue), contra-lateral side vestibule, eliminating the need for constant patient mouth rinsing and the need for a dental assistant to aspirate debris.

The fluid evacuation system 34 is comprised of the aforementioned evacuation channels and holes located in fluid evacuation members such as the tongue and cheek retractor 22, dispersion piece 24, and bite block 26. As used herein, the term "fluid evacuation member" refers to a piece that includes one or more evacuation channels for removing fluids from the patient's mouth. For example, as illustrated in FIGS. 8A and 8B, fluid is drawn from the tongue area through the evacuation holes 60 and evacuation channels 58 in the tongue retractor portion 56. This fluid is further drawn through the second main evacuation channel 82 of the dispersion piece 24, and the bite block 26, and out the vacuum tube 32. The suction drawing the fluids and debris out the vacuum tube 32 is provided by a vacuum source 110 (FIG. 1).

Figure 9:
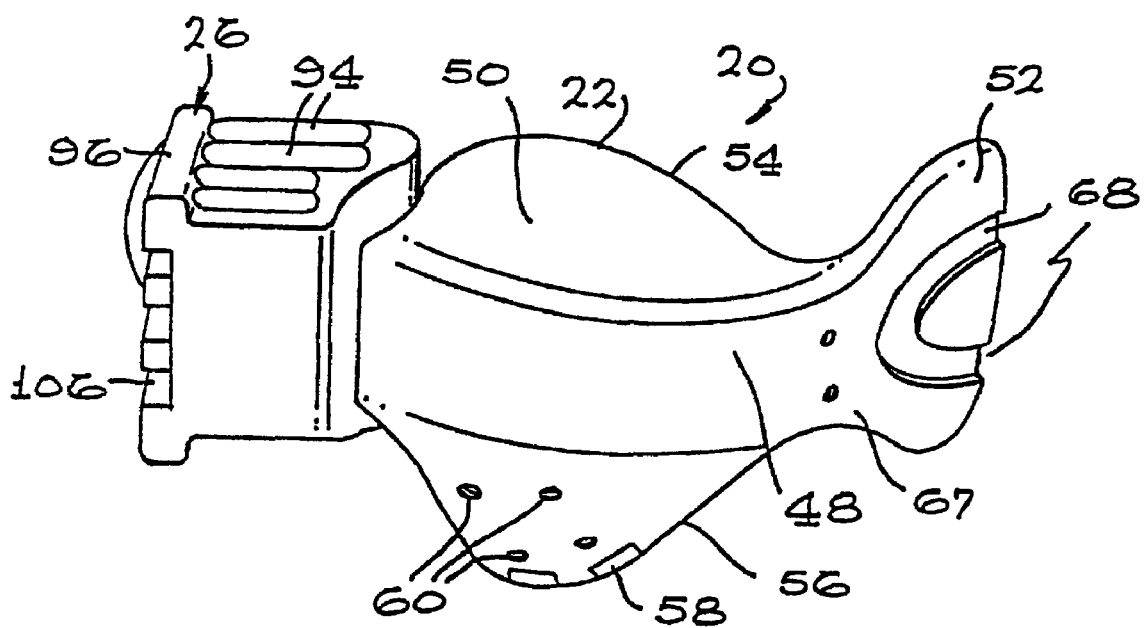
FIG. 9 is a front perspective view of an alternative preferred embodiment of the intraoral illumination device.
Figure 5:
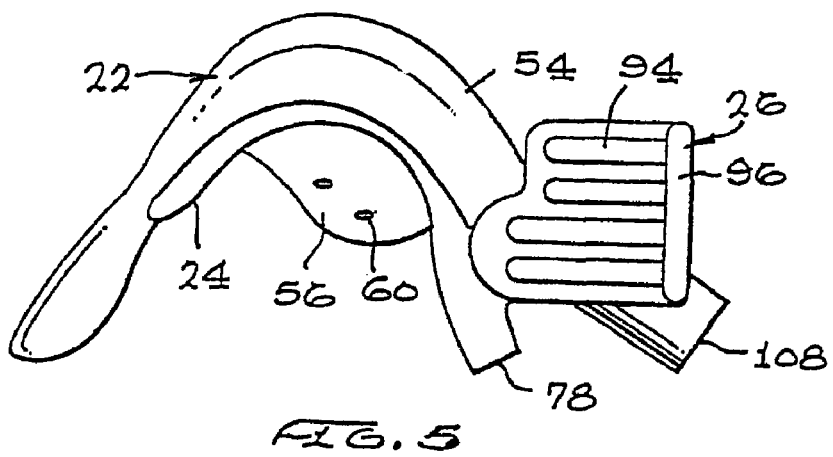
FIG. 5 is a top plan view of the intraoral illumination device illustrated in FIG. 1.
Figure 6:
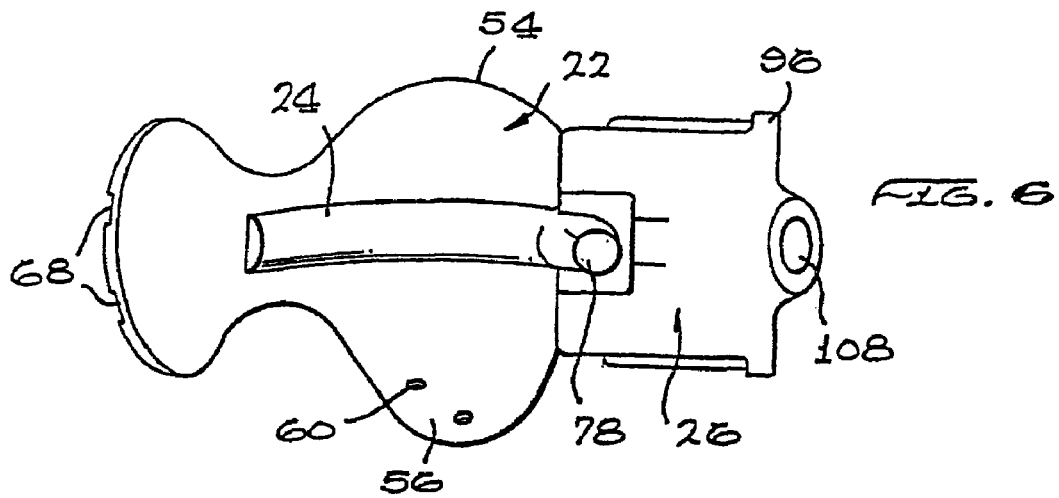
FIG. 6 is a front elevational view of the intraoral illumination device illustrated in FIG. 1.
Figure 7:
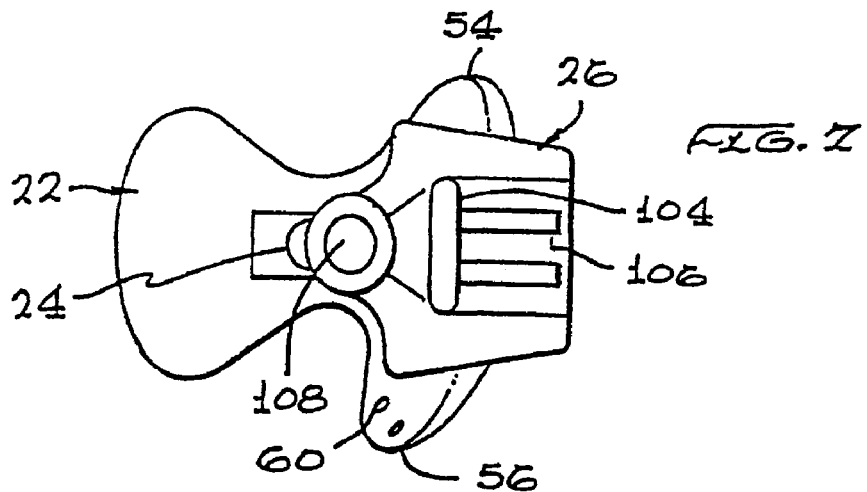
FIG. 7 is an end view of the intraoral illumination device illustrated in FIG. 1.
Figure 18A:
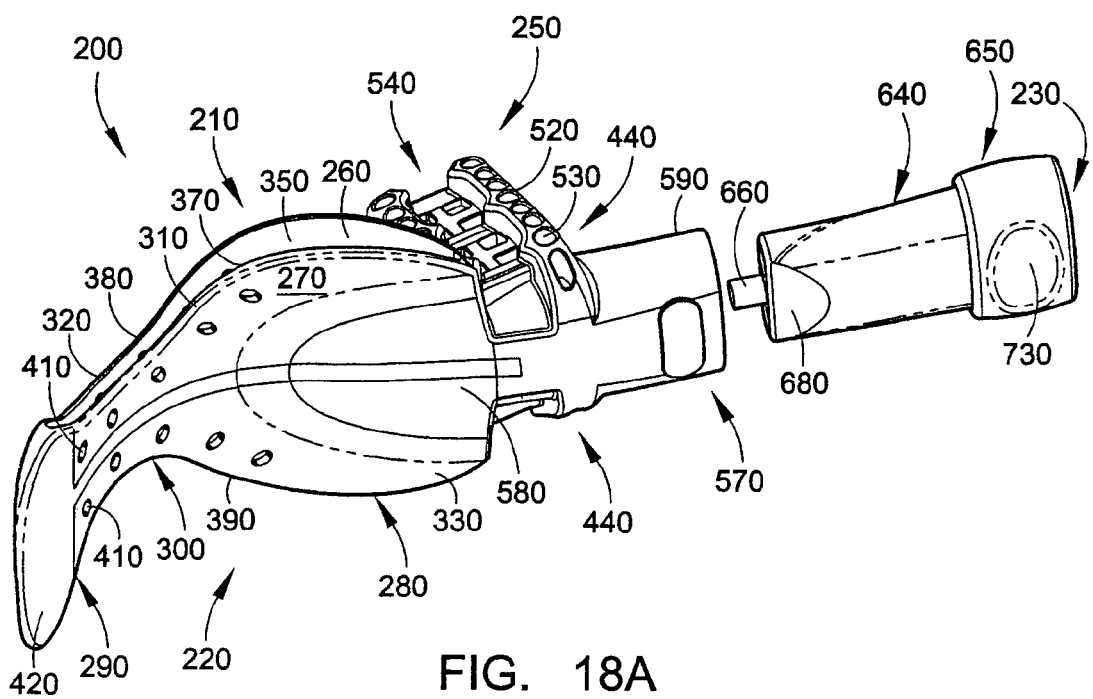
FIG. 18A is a front perspective view of a further embodiment of an intraoral illumination device in conjunction with an embodiment of an optional vacuum-only adapter shown separated from the intraoral illumination device.
Figure 18B:
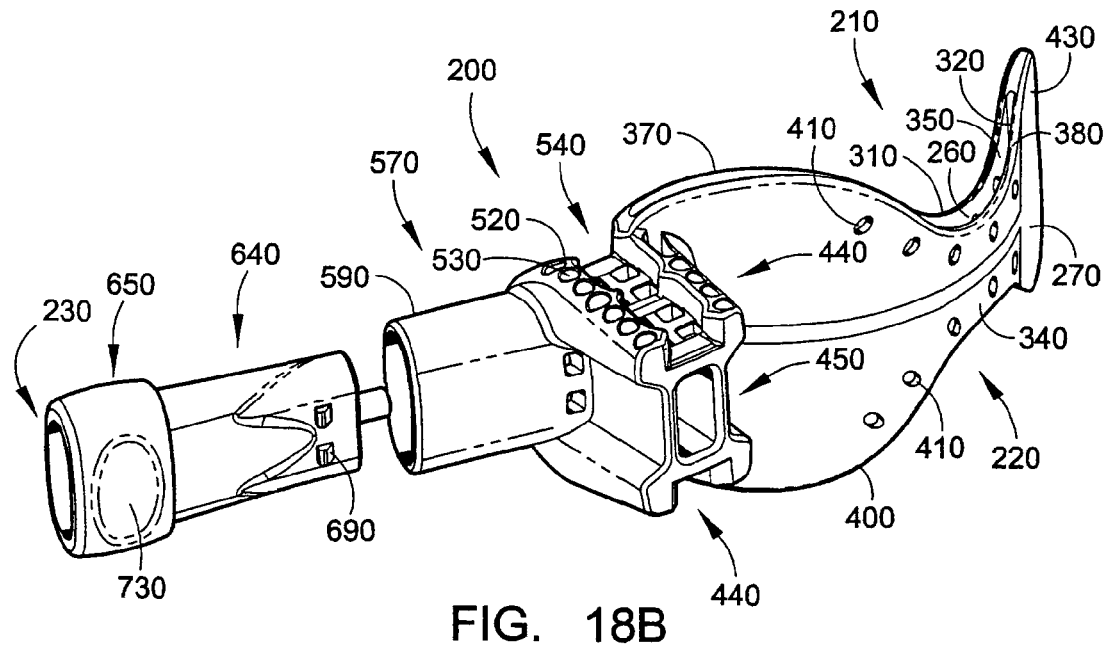
FIG. 18B is a rear perspective view of the intraoral illumination device and the optional vacuum-only adapter illustrated in FIG. 18A.

With reference to FIGS. 9 and 10, an intraoral illumination device 112 constructed in accordance with an alternative preferred embodiment of the invention will now be described. Elements of the intraoral illumination device 112 similar to those described above with respect to the intraoral illumination device 20 are referred to by common reference numbers, but with an "a" suffix, e.g., dispersion piece 24*a*. The intraoral illumination device 112 is similar to the intraoral illumination device described above, except it is adapted for use as a disposable unit, eliminating the need for sterilization and the associated costs and spread-of-disease risks. The device 112 includes an integrated bite block and light carrier/fluid evacuation tube connector 114. The connector 114 is an overmolded piece, has a bitumen configuration, and is configured to extend significantly outside of the mouth of the patient where it connects with a combined bitumen light carrier and vacuum tube 116. Because this connection between the connector 114 and combined light carrier and vacuum tube 116 is substantially outside of the patient's mouth, the combined light carrier and vacuum tube 16 can be re-used, i.e., does not have to be disposable and does not need to be autoclaved, avoiding degradation, especially of the light carrier, e.g., fiber optic bundle. As discussed above, the bite block 26*a* and dispersion piece 24*a* may be fixed relative to each other. Alternatively, as discussed above, the dispersion piece 24*a* may be pivotally connected to the bite block 26*a* in order to accommodate different size arch widths. Regardless, the bite block 26*a*, dispersion piece 24*a*, and tongue and cheek retractor 22*a* together form a single, integrated disposable piece.

With reference to FIGS. 11A and 11B, an alternative embodiment of an integrated bite block and light carrier/fluid evacuation connector 118 and combined light carrier and vacuum tube 120 are shown. In this embodiment, the light carrier portions and fluid evacuation portions are coaxially aligned.

With reference to FIGS. 12 and 13, an intraoral illumination device 122 constructed in accordance with an additional preferred embodiment of the invention will now be described. Elements of the intraoral illumination device 122 similar to those described above with respect to the intraoral illumination devices 20, 112 are referred to by common reference numbers, and with a "b" suffix. Similar to the intraoral illumination device 112 described above, the intraoral illumination device 122 is adapted for use as a disposable unit, eliminating the need for autoclaving and the associated costs and spread-of-disease risks. The device 112 preferably has a two-piece, integrated construction. The device includes a dispersion piece 124 surrounded by a tongue and cheek retractor 126.

The dispersion piece 124 is preferably made of single, rigid, light-dispersive material such as acrylic or a flexible material such as a molded flexible urethane. However, it will be readily understood by those skilled in the art that other clear, flexible or rigid materials may be used. The dispersion piece 124 has an arcuate, light-dispersing section 128, a bite block section 130, and an optical connection section 132. The light-dispersing section 128 is received within a main receiving channel 134 of the tongue and cheek retractor 126. The light-dispersing section 128 may have a composition that is varied, e.g., graduated, to control the amount of dispersion in different areas of this section 128 and evenly distribute the overall rumination. The bite block section 130 includes a generally rigid support structure for the bite block. The optical connection section 132 is configured to optically connect the light-dispersing section 128 to the light source through a light carrier such as a fiber optic bundle.

The tongue and cheek retractor 126 includes a main body section 50b, a cheek retractor portion 52b, an upper roof portion 54b, and a tongue retractor portion 56b. Fluid evacuation channels (not shown) within the tongue and cheek retractor 126 communicate with the outside of the tongue and cheek retractor (such as through evacuation holes 60b) to remove fluids from the patient's mouth. The fluid evacuation channels communicate with the main evacuation channel 134. The tongue and cheek retractor 126 includes a bite block 136 and a connection section 138. The connection section 138 is configured to extend outside of a patient's mouth and attach to a multi-lumen tube 140. The connection section 138 includes a retention barb 142. The connection section 138 also houses a pair of fluid evacuation channels 144 and the optical connection section 132.

The multi-lumen tube 140 includes fluid evacuation lumens 146 in order to communicate the fluid evacuation system in the device 122 with a vacuum source and a light carrier 148 in order to optically couple the dispersion piece 124 with a light source. The multi-lumen tube 140 includes a connector 150 for attaching the intraoral illumination device to the multi-lumen tube 140. A slot 152 in the connector 150 is configured to receive and retain the retention barb 142 when the connection section 138 is fully engaged with the multi-lumen tube 140.

With reference to FIG. 16, an embodiment of a transition mechanism 154 to transition a pre-existing light carrier 156 and a vacuum tube 158 at the health care provider's into the single, multi-lumen tube 140 is shown. The transition mechanism 154 includes the appropriate connections for attachment to pre-existing light carriers 156 and vacuum tubes 158 or may include separate connectors for interfacing between light carriers 156 and vacuum tubes 158 and the transition mechanism 154. In an alternative pre-embodiment, the transition mechanism 154 may include a light source and/or a vacuum source, eliminating the need to connect with a light carrier 156 and/or vacuum tube 158. With reference to FIG. 17, a special connector 160 may interface between the transition mechanism 154 and the multi-lumen tube 140 to further transition the transition mechanism 154 into the multi-lumen tube 140. However, it will be readily apparent to those skilled in the art how transitioning devices such as the special connector 160 may be located within the transition mechanism 154, eliminating the need for a special connector.

Together, the intraoral illumination device 122, multi-lumen tube 140, transition mechanism 154, and light source form an intraoral illumination system and the intraoral illumination device 122 in conjunction with one or more of the following form an intraoral illumination kit: the multi-lumen tube 140, the transition mechanism 154, the light source, the vacuum source, the special connector 160, and separate connector(s) for attaching light carrier 156 and/or vacuum tube 158 to the transition mechanism 154.

The method of manufacturing the intraoral illumination device will now be described. The intraoral illumination device is manufactured in a two-step process known as multi-shot injection molding. The acrylic dispersion piece 124 is molded first in a two-piece mold including a first mold having a first mold cavity and a second mold having a second mold cavity, and, then, the second mold is removed. The second mold is replaced by a third mold having a third mold cavity that has the details of the tongue and cheek retractor 126. Next, rubber is injected over the dispersion piece 124 to form the tongue and cheek retractor 126. A gas-assist injection molding process is then used to produce the fluid evacuation channels and cavities within the tongue and cheek retractor 126. Fluid evacuation holes are created in various locations of the tongue and cheek retractor 126 to provide specific area suction within a patient's mouth. The fluid evacuation holes may be created by a laser cutting process, or similar cutting process.

The multi-lumen tube 140 is extruded with the light tube 148 enclosed within the tube 140. The light tube 148 is made from a semi-flexible, solid-core plastic, optical material such as a fiber optic bundle and. is covered with a cladding such as Teflon before extrusion. With reference to FIG. 15, the multi-lumen tube 140 is extruded so as to have an elliptical shape with the light tube 148 in the center. The tube 140 is extruded so that a portion of the light tube 148 extends beyond the distal end of the multi-lumen tube 140. After extrusion, the multi-lumen tube 140 is over-molded with a custom connector 150. Alternatively, the connector 150 may be a separate piece made of a material such as stainless steel and fixed to the end of the tube 140. The connector 150 is configured to inhibit leakage and ensure a tight connection with the connection section 138 of the intraoral illumination device 122.

Thus, the intraoral illumination device of the present invention eliminates the problem of shadowing resulting from overhead light sources, single-point light sources, or other illumination sources of the past by transmitting dispersed light outwards from a rear, central part of the intraoral cavity, generally between the patient's rear teeth. The generally 180 degree arc of the dispersion piece spreads the area of illumination, eliminating shadows caused from a single point light source. The fluid evacuation system of the device vacuums oral fluids, water delivered by a dental hand piece, and debris. The fluid evacuation system prevents these fluids and debris from being aspirated or swallowed down the throat of the patient, improves the comfort of the patient, eliminates the need of the patient to continually rinse his or her mouth, and reduces the amount of spray emitted from the patient's mouth. The tongue and cheek retractor retracts and protects the cheek and tongue of the patient, helping to reduce interference between these parts of the mouth and the procedure. The bite block allows the patient to rest the muscles of mastication, eliminating the need to strain to keep his or her mouth open. Because the device simultaneously removes fluids and debris, isolates the area of interest in the mouth, and illuminates the area of interest, the time of the procedure and the need for an assistant is greatly reduced.

With reference to FIG. 18A-19E, an intraoral illumination device (hereinafter "intraoral device") 200 constructed in accordance with another embodiment of the invention will now be described. The intraoral device 200 preferably has a single-piece, integrated, homogenous-material, injection-molded construction. The intraoral device 200 is preferably injection molded out of a translucent (e.g., transparent), flexible, soft, elastic, resilient, biocompatible thermoplastic elastomer. The intraoral device 200 is also vertically symmetrical so that an upper half 210 is symmetric with respect to a lower half 220. This allows the same intraoral device 200 to be positioned on either the left side or the right side of the patient's mouth. The intraoral device 200 may also come in different sizes for different-size mouths. The intraoral device 200 is also disposable after each use.

The intraoral device 200 may be used with an optional vacuum-only adapter 230 if intraoral illumination is not desired with the intraoral device 200. Further, in an alternative embodiment of the intraoral device 200, the intraoral device 200 may not include the illumination aspects described in more detail below. In such an embodiment, the intraoral device 200 does not illuminate the patient's mouth.

The single-piece intraoral device 200 generally includes integrated tongue and cheek retractor 240, bite piece 250, and connection section 570, each of which will be described in turn below.

The tongue and cheek retractor 240 has inner surfaces 260 and outer surfaces 270. The retractor 240 includes an incurved main body portion 280 and a forwardly angled cheek retractor (or "whale tail") portion 290 joined by isthmus portion 300.

The retractor 240 includes an upper front flap 310, an upper rear flap 320, a lower front flap 330, and a lower rear flap 340. The front flaps 310, 330 and rear flaps 320, 340 are separated by upper gap 350 and lower gap 360, respectively. The flaps 320, 330, 340, 350 all extend from and share a common, central spine 365. The spine 365 extends longitudinally a majority of the length of the retractor 240 and divides the upper half 210 from the lower half 220 of the intraoral device 200. In addition to serving as the intersection location for the flaps 320, 330, 340, 350, the spine 365 may serve as a light pipe and a separator for an upper internal evacuation channel and a lower internal evacuation channel. The upper front flap 310 and upper rear flap 320 include respective S-shaped upper edges or rims 370, 380 and the lower front flap 330 and the lower rear flap 340 include respective s-shaped lower edges or rims 390, 400.

The flaps 310, 320, 330, 340 include evacuation holes 410 adjacent the edges 370, 380, 390, 400. The evacuation holes 410 in the upper flaps 310, 320 may be generally aligned with each other and communicate with an upper internal evacuation channel formed in the upper gap 350 and the evacuation holes 410 in the lower flaps 330, 340 are generally aligned with each other and communicate with a lower internal evacuation channel formed in the lower gap 360. Although twenty evacuation holes 410 are shown, the number of evacuation holes 410 and/or location of the evacuation holes 410 may vary. The upper half 210 and/or the lower half 220 may include zero or more evacuation holes 410. The number of evacuation holes 410 in the upper half 210 may be the same or different from the number of evacuation holes 410 in the lower half 220. In an alternative embodiment, the evacuation holes may not be aligned with each other.

The upper front flap 310 and the upper rear flap 320 are configured to rest or flex against the paletal area or roof of the patient's mouth 36 during use. The upper roof of the mouth spans the upper gap 350 and pushes or bends the upper front flap 310 and the upper rear flap 320 forward to created a seal along the upper edges 370, 380, creating a sealed upper internal evacuation channel in the upper gap 350. The lower front flap 330 and the lower rear flap 340 are configured to rest or flex against the lingual area of mouth or tongue to keep the tongue protected and retracted during use. The tongue and floor of the patient's mouth span the lower gap 360 and forms a seal along the lower edges 390, 400, creating a sealed lower internal evacuation channel in the lower gap 360.

The cheek retractor portion 290 has an angled, curved, generally whale-tail shape. In use, the cheek retractor portion 290 is flexed inward towards the main body portion 280 and rests against the inner cheek tissue between the cheek tissue and the outside of the teeth. With the cheek retractor portion 290 flexed, the upper flaps 310, 320 and lower flaps 330, 340 are closed together, forming a seal along the upper edges 370, 380 and the lower edges 390, 400 of the retractor 240 adjacent where the isthmus portion 300 and cheek retractor portion 290 join. A front 420 and/or rear 430 of the cheek retractor portion 290 may include texturing, detail, or a varied composition to disperse light and prevent "hot spots" that can make it difficult for the health care provider to observe the patient's mouth, or lensing (e.g., fresnel lens) to focus light on different areas of the mouth.

Figure 19A:
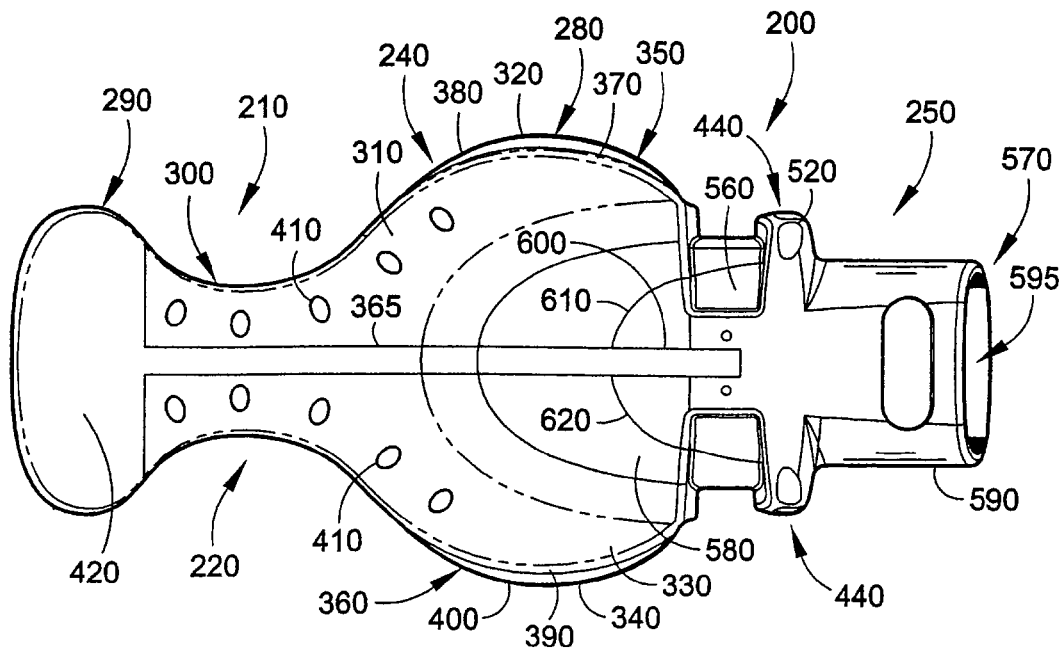
FIG. 19A is a front elevational view of the intraoral illumination device illustrated in FIG. 18A.
Figure 19B:
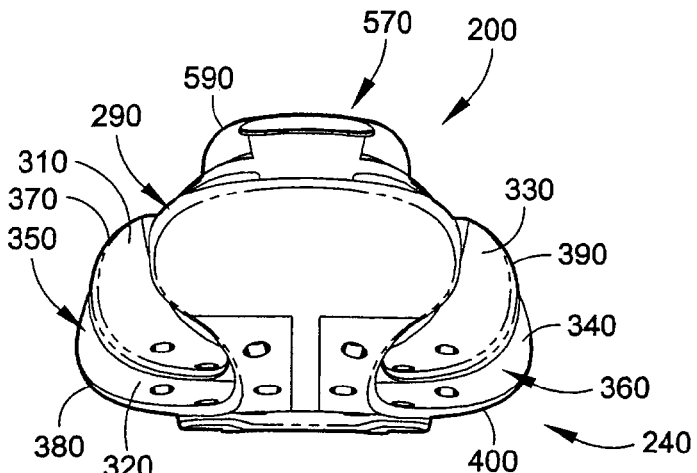
FIG. 19B is a left side elevational view of the intraoral illumination device illustrated in FIG. 18A.
Figure 19C:
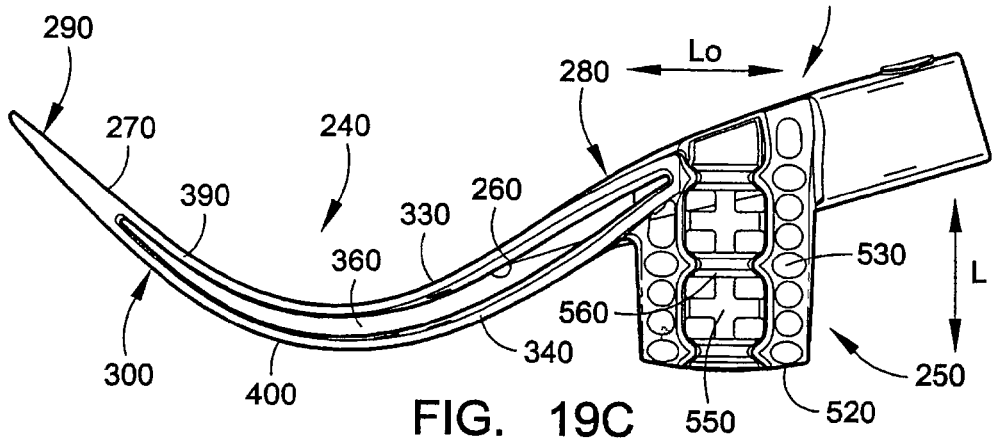
FIG. 19C is a bottom plan view of the intraoral illumination device illustrated in FIG. 18A.
Figure 19D:
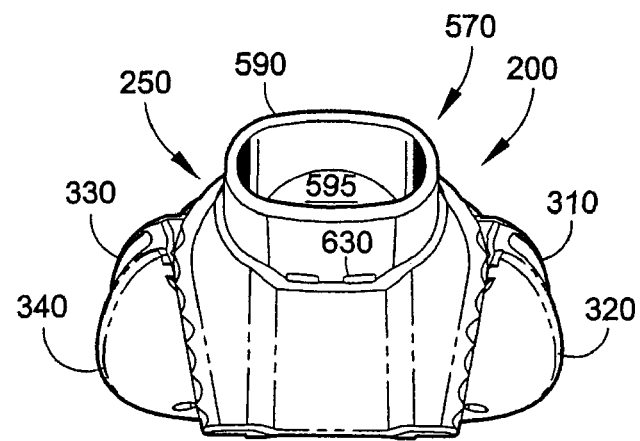
FIG. 19D is a right side elevational of the intraoral illumination device illustrated in FIG. 18A.
Figure 19E:
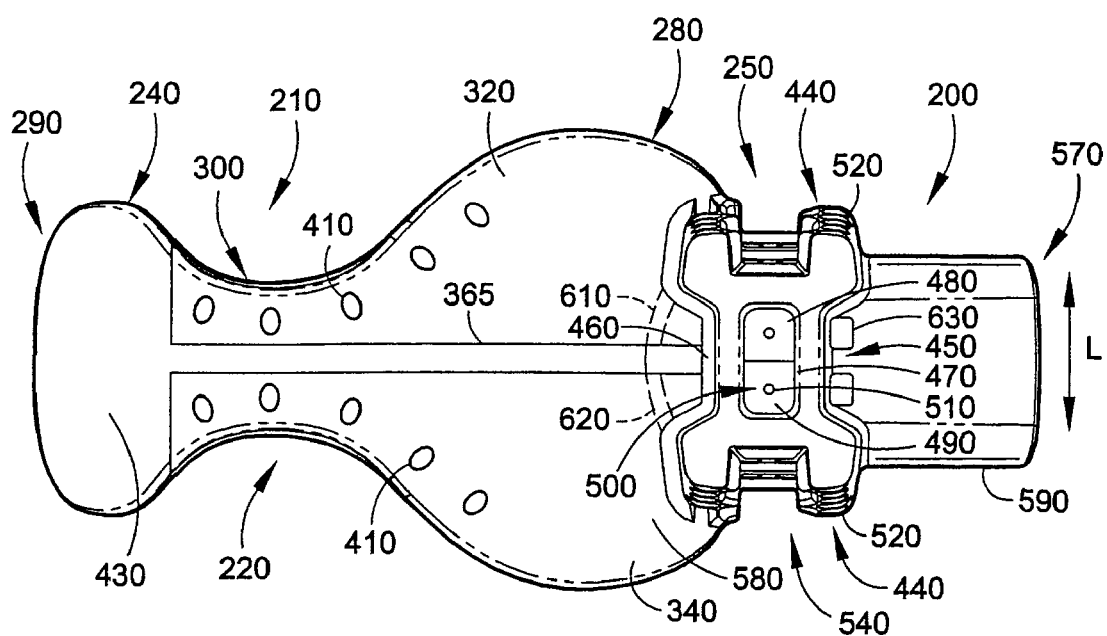
FIG. 19E is a rear elevational view of the intraoral illumination device illustrated in FIG. 18A.

With reference especially to FIGS. 19A and 19E, the cheek retractor portion 290 is shown as having a maximum height (or width) about ⅔ the maximum height (or width) of the main body portion 280. In alternative embodiments, the cheek retractor portion 290 may have smaller or larger maximum heights. For example, in an alternative embodiment, the cheek retractor portion 290 may have a whale-tail shape as shown, but with a maximum height or width substantially the same as the maximum height or width of the main body portion 280.

When the tongue and cheek retractor 240 is positioned within the patient's mouth (similar to that shown in FIG. 1), the flexed upper flaps 310, 320, the flexed lower flaps 330, 340, and the flexed cheek retractor portion 290 form an envelope for isolating an area of interest in the patient's mouth and protect the upper roof, tongue and cheek of the patient's mouth from instruments such as dental drills during the dental procedure and prevent aspiration of debris or dropped items into the patient's throat.

The bite piece 250 includes symmetric, opposite tooth-engaging portions 440 joined by an intermediate connection portion 450. The intermediate connection portion 450 is more flexible than the tooth engaging portions 440 and allows flexible, resilient, elastic movement of the tooth engaging portions 440 in vertical, longitudinal, and lateral directions with respect to each other to allow vertical, longitudinal, and lateral biting movement by the patient for maximum biting comfort. The bite piece 250 also may be moved or indexed forward and rearward a molar notch to allow for better or more comfortable posterior or anterior positioning of the bite piece 250 and intraoral device 200.

The bite piece 250 allows 0-50% vertical compressibility (i.e., the bite piece 250 may be compressed vertically when a patient bites on it from 0% of the height of the bite piece 250 to as much as 50% of the height of the bite piece in a general vertical direction V shown in FIG. 19E). In a preferred embodiment, the bite piece 250 allows at least 5% vertical compressibility, in a more preferred embodiment, the bite piece 250 allows at least 10% compressibility, and in a most preferred embodiment, the bite piece 250 allows at least 15% vertical compressibility.

The bite piece 250 allows 0-75% longitudinal displacement (i.e., displacement of one tooth-engaging portion 440

0-75% of the width of the tooth-engaging portion 440 relative to the opposite tooth engaging portion 440 in a general longitudinal direction Lo shown in FIG. 19C). In a preferred embodiment, the bite piece 250 allows at least 5% longitudinal displacement, in a more preferred embodiment, the bite piece 250 allows at least 10% longitudinal displacement, and in a most preferred embodiment, the bite piece 250 allows at least 15% longitudinal displacement of the tooth-engaging portions.

The bite piece 250 allows 0-20% lateral displacement (i.e., displacement of one tooth-engaging portion 440 0-20% of the length of the tooth-engaging portion 440 relative to the opposite tooth engaging portion 440 in a general lateral direction L shown in FIG. 19C). In a preferred embodiment, the bite piece 250 allows at least 2% lateral displacement, in a more preferred embodiment, the bite piece 250 allows at least 4% lateral displacement, and in a most preferred embodiment, the bite piece 250 allows at least 6% lateral displacement of the tooth-engaging portions.

The intermediate connection portion 450 includes two opposite vertical walls 460. Inner surfaces 470 of the two vertical walls 460, inner surfaces 480 of the tooth engaging portions 440, and an inner dividing wall 490 form a generally rectangular block-shaped suction cavity 500. The inner dividing wall 490 includes a pair of vacuum holes 510 to allow a vacuum force to be provided in the cavity 500 for suctioning fluids in the area of the retro molar pad and the maxillary tuberosity of the patient's mouth. The tooth engaging portions 440 include parallel, generally laterally extending tooth-engaging ridges 520. The tooth-engaging ridges 520 include vertically extending cylindrical chambers 530. Disposed between the ridges 520 is a groove 540. At the bottom of the groove 540 are two adjacent, vertically extending cross-shaped members 550. Vertically extending dividers 560 are disposed at ends of the cross-shaped members 550. The cross-shaped members 550 and the vertically extending dividers 560 are biting surfaces that may be engaged by the bottom of the top teeth and the top of the bottom teeth to help keep the bite piece 250 in position.

The connection section 570 extends from the bite piece 250 and a proximal portion 580 of the retractor 240. The connection section 570 is configured to extend outside of a patient's mouth and attach to a multi-lumen tube for delivering illumination and vacuum suction to the intraoral device 200 (or the vacuum-only adapter 230 for delivering only vacuum suction to the intraoral device 200).

The connection section 570 includes an open-ended tube 590 having a generally elliptical cross-section that tapers slightly in height as the tube 590 intersects the bite piece 250 and the proximal portion 580 of the retractor 240. An interior of the open-ended tube 590 defines a main vacuum channel 595. Adjacent the bite piece 250 and the proximal portion 580 of the retractor 240, the connection section 570 includes a cylindrical tube-shaped illumination connector 600 for transmitting light to the spine 365 and for supporting the plug portion 640 or other plug. On opposite vertical sides of the illumination connector 600, where the illumination connector 600 joins the proximal portion 580 of the retractor 240, upper and lower vacuum ports 610, 620 communicate the main vacuum channel 595 with the upper and lower internal evacuation channels of the retractor 240. The main vacuum channel 595 communicates with the suction cavity 500 through the vacuum holes 510 in the inner dividing wall 490. The wall of the tube 590 includes a pair of adjacent, vertically spaced slots 630 for retaining corresponding retention barbs in the plug portion 640 of the vacuum-only adapter 230.

With reference to FIGS. 20A-20E, the vacuum-only adapter 230 will now be described in more detail. The adapter 230 includes a plug portion 640 and a handling portion 650.

The plug portion 640 includes a generally elliptical outer cross-section that is slightly smaller in dimension than the generally elliptical cross-section of the tube 590 so that the tube 590 may slidingly receive the plug portion 640. A cylindrical plug 660 slightly smaller in dimension than the inner dimension of the illumination connector 600 extends from a distal end 670 of the adapter 230. The cylindrical plug 660 is matingly received by the illumination connector 600 when the plug portion 640 is plugged into the tube 590. The plug portion 640 includes a beveled surface 680 adjacent the distal end 670. When the plug portion 640 is plugged into the tube 590, the beveled surface 680 engages a corresponding angled surface within the connection section 570. Thus, the beveled surface 680 may be used to ensure that the adapter 230 is properly oriented when plugged into the connection section 570. With the plug portion 640 plugged into the connection section 570, the plug portion 640 helps to keep the bite piece 250 from collapsing in the front. A pair of barbs 690 extend from the plug portion 640 on a side opposite from the beveled surface 680. When the plug portion 640 is plugged into the tube 590, the barbs 690 engage the corresponding slots 630 in the connection section 570 to retain the adapter 230 in the connection section 570. A pair of vacuum lumens 700 extend longitudinally within the adapter 230, along the cylindrical plug 660. Near a proximal end 710 of the adapter 230, each vacuum lumen 700 may terminate in a receiver 720 for receiving cylindrical vacuum lines of a vacuum hose.

The handling portion 650 may have an overall dimension slightly larger than the dimension of the plug portion 640 and include opposite incurved sides 730 to facilitate handling of the handling portion 650 with one's fingers.

One or more further embodiments of the intraoral device may include one or more of the implementations described immediately below.

A separate plug, adapter, or tube having one or more LEDs may plug into the connection section of the intraoral device for illuminating the intraoral device.

The plug, adapter, or tube may include suitable electronics to control intensity of light from the one or more LEDs.

A slidable/movable filter may be employed with a separate curing light. The movable filter may be moved to a first position to filter out light that causes composite filling material to cure, preventing curing, and moved away from this position to allow light from the curing light to cure the composite filling material.

The plug, adapter, or tube may include a suction control mechanism that provides upper and lower evacuation channel control to control suction to the upper evacuation channel, the lower evacuation channel or both evacuation channels of the intraoral device.

The plug, adapter, or tube may include temperature control (e.g., through the use of one or more temperature sensors such as a thermistor) to turn off or turn down the one or more LEDs if the temperature in the region becomes too high. For example the one or more LEDs may be turned down to a lower intensity and heat level. When the one or more LEDs are sufficiently cooled to a desired temperature by the fluid cooling system described below, the one or more LEDs may be turned up to a higher intensity or normal level. In addition to or instead of lowering the one or more LEDs, the fluid cooling system may increase cooling (e.g., increase flow rate, decrease temperature level of cooling fluid) of the one or more LEDs if it is determined that the temperature in the region becomes too high.

A proximal end of the tubing used to deliver vacuum suction, electricity, and cooling fluid may include a plug-in hook up or connector to connect to vacuum, electricity, and water sources. Adjacent a proximal end of the tubing, an on/off switch may be located to actuate vacuum suction, electricity, and/or cooling fluid flow.

Using one or more LED's as the light source for the intraoral device in the manner described above eliminates the need for lengthy and heavy fiber optics and allows the tubing to drop 90 degrees from patient's mouth to the floor. This eliminates the leverage and pulling on the side of the patient's mouth caused by lengthy and heavy fiber optics in the past; fiber optics can't be bent at sharp 90 degree angles.

The plug, adapter, or tube may include a heat sink for removing heat emitted from the one or more LEDs. An example heat sink may include a fluid cooling system that circulates a cooling fluid (e.g., water) in the area of the one or more LEDS. For example, vacuum tubing that includes one or more vacuum lumens to remove fluid from the patient's mouth may also carry a cooling fluid delivery lumen for delivering cooling fluid to the region of the one or more LEDs. After removing heat from the region of the one or more LEDs, the cooling fluid may be withdrawn through the one or more vacuum lumens. In another embodiment of the heat sink, which is also applicable to the heat sink device 800 described below, a thermostat or temperature control may be used with the heat sink fluid cooling system so that cooling may be automatically controlled. For example, but not by way of limitation, the flow rate of the cooling fluid through the fluid cooling system may be increased/decreased, the temperature of the cooling fluid may be increased/decreased, and/or the cooling fluid may be caused to circulate/recirculate through the heat sink and the fluid cooling system and withdrawn on a as-needed basis. The same or a different thermostat or temperature control may be used for controlling the intensity/heat level of the one or more LEDs as described further above.

For example, with reference to FIGS. 21 and 22, a combined illumination, aspiration and heat sink device (hereinafter heat sink device 800) for use with an intraoral illumination device for providing the heat sink function (and other functions) will be described. The heat sink device 800 will described as being used with the intraoral illumination device 200 described above with respect to FIGS. 18A-19E; however, the heat sink device 800 may be used with other intraoral illumination devices such as, but not limited to, the other intraoral illumination devices shown and described herein. Further, the heat sink device 800 may be used in applications where vacuum suction cooling of a heat-emitting illumination device is desired, other than for intraoral illumination and aspiration applications. Still further, the heat sink device 800 may be used for applications where a cooling fluid under positive pressure (not vacuum pressure) is used. Thus, in another embodiment of the heat sink device 800 and method described below, the cooling fluid is circulated and/or recirculated through the device 800 under positive pressure (not negative, vacuum pressure).

The heat sink device 800 includes an illumination and vacuum suction head 810, a main body housing 820, which houses a removable illumination stick 830, a heat sink member 840, and a valve body 850, and a lower body housing 860. The illumination and vacuum suction head 810, the main body housing 820, and the valve body 850 are made of an autoclavable hard plastic or metal material. Each of these elements will be described in turn below.

The illumination and vacuum suction head 810 includes a light pipe 870 and a plug housing 880. The plug housing 880 houses the light pipe 870 and internal fluid channels (not shown). A plug portion 890 includes a generally cylindrical configuration with flat sidewalls 900. The exposed end of the light pipe 870 is cylindrical and includes a slightly smaller dimension than the inner dimension of the illumination connector 600 (FIG. 19A) so as to be matingly received therein when the plug portion 890 is plugged into the tube 590. A rear portion 910 of the head 810 is angled approximately 90 degrees from the plug portion 890. The rear portion 910 includes a hole 915 that receives a head 930 of the removable illumination stick 830.

The removable illumination stick 830 includes an elongated narrow body 920, which is housed within the main body housing 820 and connected to the head 930. The head 930 carries one or more illumination sources. In the embodiment shown, the illumination source is a single white LED 940. The LED 940 is bonded or soldered to a copper plate 950, which is attached to a heat transfer plate 960 carried by the body 920. The body 920 also carries suitable electronics for operating the LED 940. The illumination stick 830 includes a touch pad resistor or mechanical switch on its rear side for controlling the intensity level of the LED 940.

The heat sink member 840 includes an elliptical transfer plate heat sink 970. The heat sink 970 includes a central hole 980 configured to receive and engage the body 920 and heat transfer plate 960 of the illumination stick 830. Integrated with the heat sink 970 are cooling tubes 990. Top ends of the cooling tubes 990 mate with the internal fluid channels of the illumination and vacuum suction head 810. Fasteners 1000 may be used to fix the heat sink member 840 and the illumination stick 830 to the vacuum suction head 810 and the main body housing 820. The heat sink member 840 and the illumination stick 830 may be removable for cleaning, sterilizing, and autoclaving.

The main body housing 820 is hollow and includes a slightly curved frustoconical configuration. The main body housing 820 houses the removable illumination stick 830, the heat sink member 840, and the valve body 850. Valve handles 1010 are pivotally connected to the main body housing 820 and operably coupled with the valve body 850 for controlling flow therethrough. When the heat sink device 800 is in use, the valve handles 1010 are located adjacent the patient's mouth so that the patient can control suction of saliva from the patient's mouth. Movement of one of the valve handles 1010 controls suction through the upper internal evacuation channel of the intraoral illumination device 200 (FIG. 19A) and movement of the other valve handle 1010 controls suction through the lower internal evacuation channel of the intraoral illumination device 200. Movement of one of the valve handles 1010 to an open position allows suction through the upper internal evacuation channel. Movement of the same valve handle 1010 to a closed position prevents suction through the upper internal evacuation channel. Controlling local suction in this manner is important for increasing patient comfort. Suction pulling across the teeth can result in pain and increased sensitivity. More local suction in the bottom of the patient's mouth, where it is needed most, eliminates uncomfortable suction across the patient's upper teeth when it is not needed. In dental offices with insufficient vacuum pressure, this also provides more local suction in the bottom of the patient's mouth, where it is needed most. Movement of the other valve handle 1010 to an open position allows suction through the lower internal evacuation channel. Movement of the same valve handle 1010 to a closed position prevents suction through the lower internal evacuation channel. Each valve handle 1010 may be opened, closed, or partially opened to provide extensive suction control in the intraoral illumination device 200.

In the embodiment of the heat sink device 800 shown, upper and lower suction change relationship when the heat sink device 800 is used on the other side of the patient's mouth. The vacuum control handles 1010 change the off/on position from handles 1010 down/off to handles 1010 up/off because through holes are orientated at 45 degrees from the centerline of the handles 1010.

The valve body 850 is generally cylindrical and includes an upper body portion 1020, an annular flange 1030, and lower body portion 1040. The upper body portion 1020 includes internal fluid channels 1050 that matingly receive the bottom ends of the cooling tubes 990. The fluid channels 1050 communicate with valve chamber 1060. Valve member(s) (not shown) are operably associated with the valve chamber 1060 and the valve handles 1010 for controlling suction through the internal evacuation channels of the intraoral illumination device 200 in the manner described above. Below the valve chamber 1060 is a single internal fluid chamber, which runs from the valve chamber 1060 to the bottom end of the lower body portion 1040.

The lower body housing 860 is cylindrical and includes an annular recessed ledge 1070 at an upper end and a cylindrical vacuum tube 1080 at a lower end. Wires 1090, which communicate a power source (not shown) with the electronics and LED 940 of the removable illumination stick 830 for powering the same, run inside the vacuum tube 1080. The lower body portion 1040 of the valve body 850 mates with the cylindrical vacuum tube 1080. The vacuum tube 1080 is in communication with a vacuum source (not shown) to provide vacuum suction for the heat sink device 800. A commutator board 1100 is disposed between the recessed ledge 1070 and the annular flange 1030 of the valve body 850. The commutator board 1100 includes two concentric circular tracks that radially offset spring probes 1110 extend upwardly through for electrically communicating wires 1090 with the commutator board 1100. This configuration allows the lower body housing 860 to turn relative to the rest of the heat sink device 800 without putting the heat sink device 800 under torsional stress. The commutator board 1100 includes contact pins that a bottom of the illumination stick 830 is electrically coupled to.

Although not shown, in another embodiment of the invention, the heat sink device 800 may be controlled by a remote control and a wireless connection. The remote control may wirelessly communicate with the heat sink device 800 through a radio frequency (RF) link. The wireless link may include but not by way of limitation, a Blue Tooth link, an infrared link, and a wireless data network link. In alternative embodiments, the remote control may have a wired connection to the heat sink device 800. In further embodiments, the heat sink device 800 is voice operated, or control features may be integrated with a dental chair or other dental equipment for controlling the heat sink device 800. In the embodiment where the heat sink device 800 is controlled wirelessly through a RF remote control, the remote control may be pointed into or towards the patient's mouth for controlling, but not by way of limitation, the illumination level in the patient's mouth, the areas of aspiration in the patient's mouth, the amount or flow rate of aspiration, and/or the cooling/temperature level of the fluid cooling system and/or one or more LEDs.

The heat sink device 800 will now be described in use. The heat sink device 800 is connected to the intraoral illumination device 200 by plugging the plug portion 890 into the tube 590. This causes the light pipe 870 to be plugged into the illumination connector 600. This may be done before or after the intraoral illumination device 200 is inserted into the patient's mouth.

The vacuum source and the power source are activated. The vacuum source creates vacuum suction in the heat sink device 800. This causes fluid and other debris to be sucked from the patient's mouth, through the intraoral illumination device 200, and into the heat sink device 800. Movement of one of the valve handles 1010 to an open position allows suction through the upper internal evacuation channel; movement of the same valve handle 1010 to a closed position prevents suction through the upper internal evacuation channel; movement of the other valve handle 1010 to an open position allows suction through the lower internal evacuation channel; and movement of the same valve handle 1010 to a closed position prevents suction through the lower internal evacuation channel. Closing one valve handle 1010 and opening the other valve handle 1010 will create a greater suction force in the upper channel or lower channel than if both valve handles 1010 were open. Thus, each valve handle 1010 may be opened, closed, or partially opened to provide extensive suction control in the intraoral illumination device 200.

The light level in the intraoral illumination device 200 is controlled by pressing the button or touch sensor on the rear of the main body housing 820, over the touch pad resistor switch, one or more times. For example, pressing once may activate the LED 940 and set the LED 940 at a low intensity level. Pressing the rear of the main body housing 820 one or more additional times may cause the LED 940, and, hence, the inside of the patient's mouth, to become increasingly brighter.

During use of the heat sink device 800, heat is emitted by the LED 940. This heat is transferred via the heat transfer plate 960 to the transfer plate heat sink 970 of the heat sink member 840. The heat is then transferred via the cooling tubes 990 to the aspirated fluid flowing under negative pressure through the cooling tubes 990. This negative pressure fluid is removed from the heat sink member 840 by the vacuum source. Thus, the heat sink device 800 utilizes the fluid suctioned out of the patient's mouth to remove heat from (and cool) the LED 940.

Figures 21, 22:
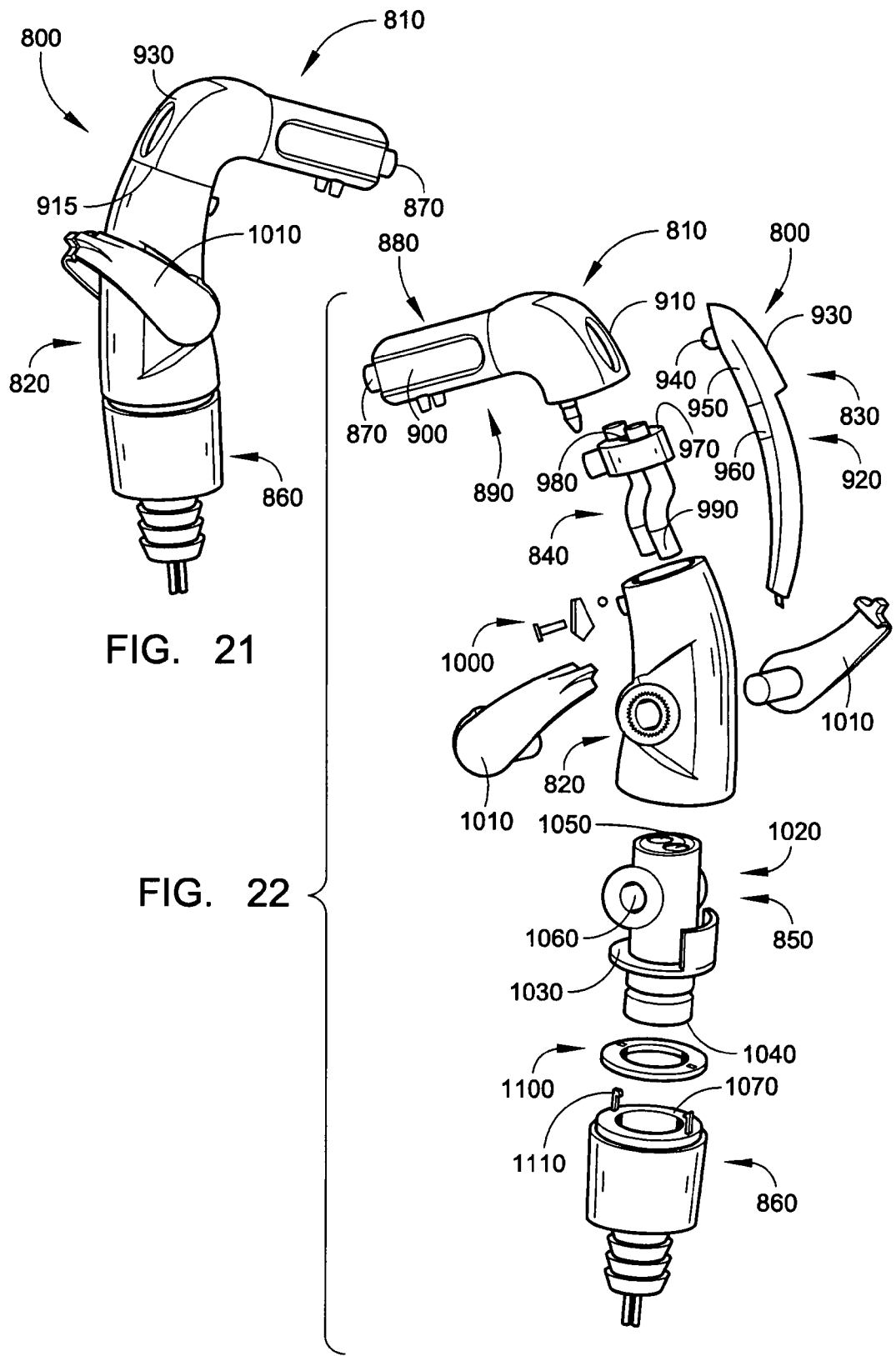
FIG. 21 is a rear perspective view of an embodiment of a combined illumination, aspiration and heat sink device for use with an intraoral illumination device.
FIG. 22 is an exploded perspective view of the combined illumination, aspiration and heat sink device illustrated in FIG. 21

To sterilize the heat sink device 800, the heat sink device 800 is disassembled into the components shown in FIG. 22, the light stick 920 is removed so no aspirated fluid comes in contact with the light stick 920, and the components of the heat sink device 800 are placed in an autoclave and sterilized.

In an alternative embodiment of the invention, the light stick 920 may be autoclaved together with the other components of the heat sink device 800 so that separation will not be necessary.

In a further embodiment of the invention, the heat sink device 800 is disposable. For example, the heat sink device 800 may be designed for single use (or a fixed number of uses), and than disposed of.

Although the heat sink device 800 is described above as including a removable illumination stick 830 with a white LED 940 as the one or more illumination sources for a general visibility application, in alternative embodiments of the invention, the removable illumination stick 830 may be replaced in the heat sink device 800 with different illumination sticks 830 with different LED's for performing different functions (e.g., bleaching, curing or oral diagnosis, and oral cancer screenings). Different illumination sticks 830 may have different wavelength illuminators, timing functions, and data logging functions. For example, but not by way of limitation, another embodiment of a removable illumination stick 830 may include one or more blue LEDs (and/or one or more white LEDs) for curing and/or tooth whitening/bleaching applications. The same or a different illumination stick 830 may be used for transluminating teeth in the patient's mouth. Another illumination stick 830 may include an amber LED combined with a curing LED for non-curing safe light. For example, the curing LED could be used for curing while the other LED is off, and then the other LED could be used for non-curing safe light for general illumination while the curing LED is off. Also, the illumination stick 830 may include a single, multi-colored LED that is controlled to provide whatever light is needed for the application desired. For example, the single, multi-colored LED may be controlled to provide the light need for curing and then later controlled to provide the light needed for general illumination. The electronics (e.g., microprocessor) in the illumination stick 830 may control the time and other parameters of the illumination aspect of each application procedure. The heat sink device 800 includes data logging functions to collect usage data such as total time used and how long the device is used at a time. This data logging is helpful for trouble shooting any problems with the heat sink device 800.

Although the illumination stick 830 is described as being replaceable, in alternative embodiments, the illumination stick 830 may be permanently attached in the heat sink device 800.

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. An intraoral illumination system, comprising:
   an intraoral illumination device including a flexible body having means for biting and retaining the intraoral illumination device in a fixed position in a patient's mouth, means for delivering illumination for illuminating the patient's mouth, means for aspirating fluids and oral debris from the patient's mouth, means for retracting and protecting a cheek of the patient on a side of the mouth opposite the biting and retaining means, and means for connecting the aspirating means and the illumination delivering means to a heat sink device, the connecting means configured to extend both within and outside the patient's mouth; and
   a heat sink device detachably connectable to the connecting means of the intraoral illumination device outside the patient's mouth, the heat sink device including means for emitting light and heat for illuminating the illumination delivering means of the intraoral illumination device, means for transferring aspirated fluid from the aspirating means of the intraoral illumination device, and heat sink means thermally coupled to the light and heat emitting means and the aspirated fluid transferring means for transferring heat away from the light and heat emitting means.

2. The intraoral illumination system of claim 1, wherein the intraoral illumination device is a one-piece, injection-molded intraoral device with a one-piece, flexible, injection molded body made of a single homogeneous material.

3. The intraoral illumination system of claim 1, wherein the heat sink device includes an illumination and vacuum suction head with a light pipe that connects with the connecting means of the intraoral illumination device for transmitting light from the light and heat emitting means of the heat sink device to the illumination delivering means of the intraoral illumination device and for transferring aspirated fluid from the aspirating means of the intraoral illumination device.

4. The intraoral illumination system of claim 1, wherein the heat sink device includes a removable illumination stick with the light and heat emitting means and electronics for operating the illumination device.

5. The intraoral illumination system of claim 4, wherein the light and heat emitting means of the illumination stick is one or more LEDs.

6. The intraoral illumination system of claim 1, wherein the heat sink device includes means for controlling flow through the aspirated fluid means.

7. An intraoral illumination system, comprising:
   an intraoral illumination device including a flexible body having means for biting and retaining the intraoral illumination device in a fixed position in a patient's mouth, means for delivering illumination for illuminating the patient's mouth, means for aspirating fluids and oral debris from the patient's mouth, means for retracting and protecting a tongue of the patient, and means for connecting the aspirating means and the illumination delivering means to a heat sink device, the connecting means configured to extend both within and outside the patient's mouth; and
   a heat sink device detachably connectable to the connecting means of the intraoral illumination device outside the patient's mouth, the heat sink device including means for emitting light and heat for illuminating the illumination delivering means of the intraoral illumination device, means for transferring aspirated fluid from the aspirating means of the intraoral illumination device, and heat sink means thermally coupled to the light and heat emitting means and the aspirated fluid transferring means for transferring heat away from the light and heat emitting means.

8. An intraoral illumination system, comprising:
   an intraoral illumination device including a flexible body having means for biting and retaining the intraoral illumination device in a fixed position in a patient's mouth, means for delivering illumination from a rear part of the patient's mouth towards a front part of the patient's mouth, eliminating shadowing, means for aspirating fluids and oral debris from the patient's mouth, and means for connecting the aspirating means and the illumination delivering means to a heat sink device, the connecting means configured to extend both within and outside the patient's mouth; and
   a heat sink device detachably connectable to the connecting means of the intraoral illumination device outside the patient's mouth, the heat sink device including means for emitting light and heat for illuminating the illumination delivering means of the intraoral illumination device, means for transferring aspirated fluid from the aspirating means of the intraoral illumination device, and heat sink means thermally coupled to the light and heat emitting means and the aspirated fluid transferring means for transferring heat away from the light and heat emitting means.

9. An intraoral illumination system, comprising:
   an intraoral illumination device including a flexible body having means for biting and retaining the intraoral illumination device in a fixed position in a patient's mouth, means for delivering illumination for illuminating the patient's mouth, means for isolating a patient's teeth on a side of the user's mouth opposite the biting and retaining means, means for aspirating fluids and oral debris from the patient's mouth, and means for connecting the aspirating means and the illumination delivering means to a heat sink device, the connecting means configured to extend both within and outside the patient's mouth; and a heat sink device detachably connectable to the connecting means of the intraoral illumination device outside the patient's mouth, the heat sink device including means for emitting light and heat for illuminating the illumination delivering means of the intraoral illumination device, means for transferring aspirated fluid from the aspirating means of the intraoral illumination device, and heat sink means thermally coupled to the light and heat emitting means and the aspirated fluid transferring means for transferring heat away from the light and heat emitting means.

* * * * *